(12) United States Patent
Humphrey

(10) Patent No.: US 10,521,657 B2
(45) Date of Patent: Dec. 31, 2019

(54) ADAPTIVE ASYMMETRICAL SIGNAL DETECTION AND SYNTHESIS METHODS AND SYSTEMS

(71) Applicant: Li-Cor, Inc., Lincoln, NE (US)

(72) Inventor: Patrick G. Humphrey, Lincoln, NE (US)

(73) Assignee: LI-COR, Inc., Lincoln, NE (US)

(*) Notice: Subject to any disclaimer, the term of this patent is extended or adjusted under 35 U.S.C. 154(b) by 0 days.

(21) Appl. No.: 16/179,705

(22) Filed: Nov. 2, 2018

(65) Prior Publication Data

US 2019/0087633 A1  Mar. 21, 2019

Related U.S. Application Data

(63) Continuation-in-part of application No. 15/914,737, filed on Mar. 7, 2018, now Pat. No. 10,151,781, (Continued)

(51) Int. Cl.
*G06K 9/00* (2006.01)
*G01R 13/00* (2006.01)
(Continued)

(52) U.S. Cl.
CPC .......... *G06K 9/0053* (2013.01); *G01N 27/00* (2013.01); *G01R 13/00* (2013.01); *G06F 11/3466* (2013.01); *G06K 9/00503* (2013.01); *G01R 23/16* (2013.01); *G06T 2207/20182* (2013.01); *G10L 21/0272* (2013.01)

(58) Field of Classification Search
CPC .. G06K 9/0053; G06K 9/00503; G01R 13/00; G01R 23/16; G06F 11/3466; G06T 2207/20182
See application file for complete search history.

(56) References Cited

U.S. PATENT DOCUMENTS 5,832,119 A  11/1998 Rhoads
6,018,312 A   1/2000 Haworth
(Continued)

OTHER PUBLICATIONS

International Search Report and Written Opinion in PCT/US2017/037393 dated Aug. 25, 2017.
(Continued)

*Primary Examiner* — Kenny A Cese
(74) *Attorney, Agent, or Firm* — Leydig, Voit & Mayer, Ltd.; Gerald T. Gray

(57) ABSTRACT

Systems and methods for detecting, decoupling and quantifying unresolved signals in trace signal data in the presence of noise with no prior knowledge of the signal characteristics (e.g., signal peak location, intensity and width) of the unresolved signals. The systems and methods are useful for analyzing any trace data signals having one or multiple constituent signals, including overlapping constituent signals, and particularly useful for analyzing data signals which often contain an unknown number of constituent signals with varying signal characteristics, such as peak location, peak intensity and peak width, and varying resolutions and varying amounts of asymmetry. A general signal model function is assumed for each unknown, constituent signal in the trace signal data.

24 Claims, 48 Drawing Sheets

Related U.S. Application Data which is a continuation-in-part of application No. 15/185,983, filed on Jun. 17, 2016, now Pat. No. 9,971,936.

(60) Provisional application No. 62/533,430, filed on Jul. 17, 2017.

(51) Int. Cl.
*G06F 11/34* (2006.01)
*G01R 23/16* (2006.01)
*G01N 27/00* (2006.01)
*G10L 21/0272* (2013.01)

(56) References Cited

U.S. PATENT DOCUMENTS

| | | |
|---|---|---|
| 6,137,831 A | 10/2000 | Johnson |
| 7,318,035 B2 | 1/2008 | Andersen et al. |
| 7,429,860 B2 | 9/2008 | Taylor et al. |
| 9,218,652 B2 | 12/2015 | Humphrey |
| 9,286,186 B2 | 3/2016 | Weiss et al. |
| 9,384,538 B2 | 7/2016 | Humphrey |
| 9,536,540 B2 | 1/2017 | Avendano et al. |
| 9,971,936 B2 | 5/2018 | Humphrey |
| 10,151,781 B2 | 12/2018 | Humphrey |
| 2004/0098208 A1 | 5/2004 | Reeve et al. |
| 2005/0059046 A1* | 3/2005 | LaBrenz ............ G16B 30/00 435/6.11 |
| 2006/0178849 A1 | 8/2006 | Maier et al. |
| 2006/0200035 A1 | 9/2006 | Ricci et al. |
| 2007/0064956 A1 | 3/2007 | Iwata |
| 2007/0150213 A1 | 6/2007 | Kim et al. |
| 2008/0306694 A1 | 12/2008 | Izmailov et al. |
| 2011/0267340 A1 | 11/2011 | Kraus et al. |

OTHER PUBLICATIONS

International Search Report and Written Opinion in PCT/US2018/042484 dated Nov. 7, 2018.
U.S. Appl. No. 15/185,983, filed Jun. 17, 2016.
U.S. Appl. No. 15/914,737, filed Mar. 7, 2018.

\* cited by examiner

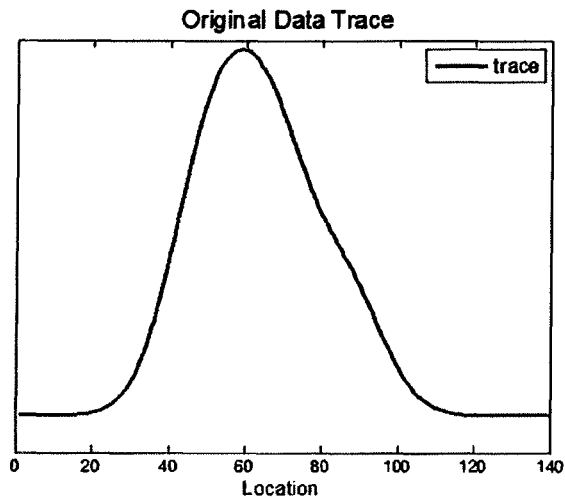
FIG. 8A
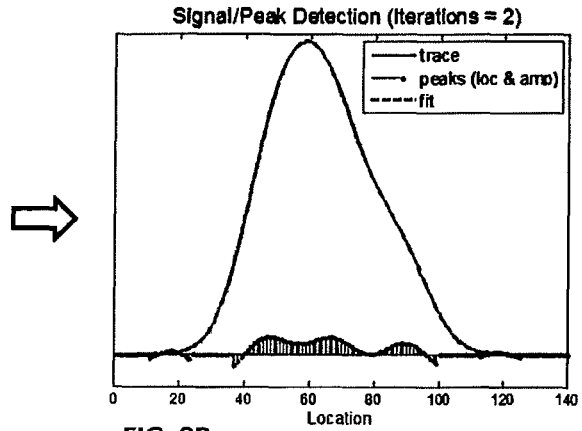
FIG. 8B
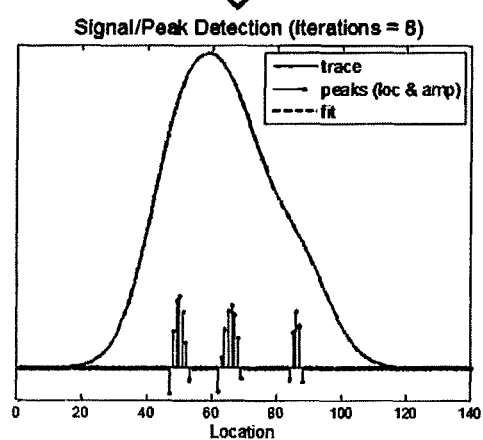
FIG. 8C
FIG. 8E
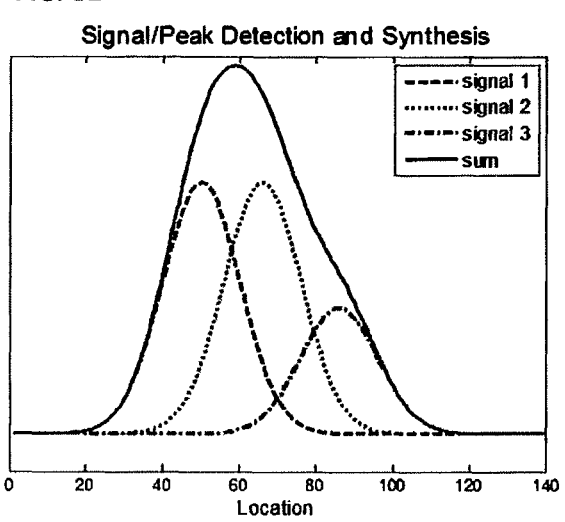
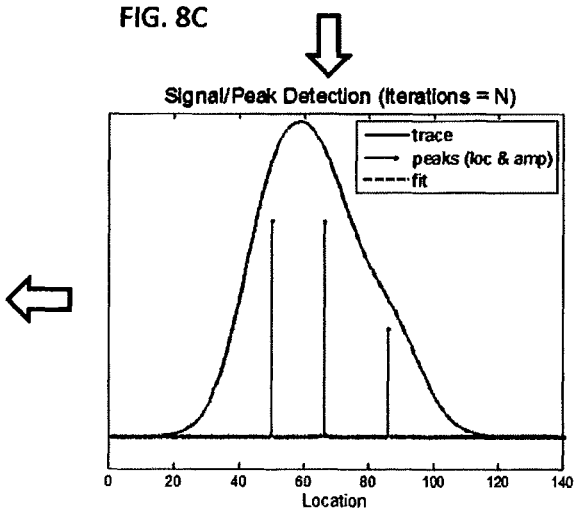
FIG. 8D

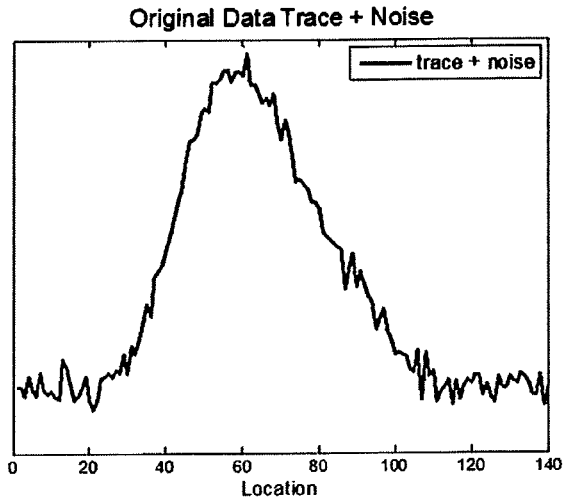
FIG. 9A
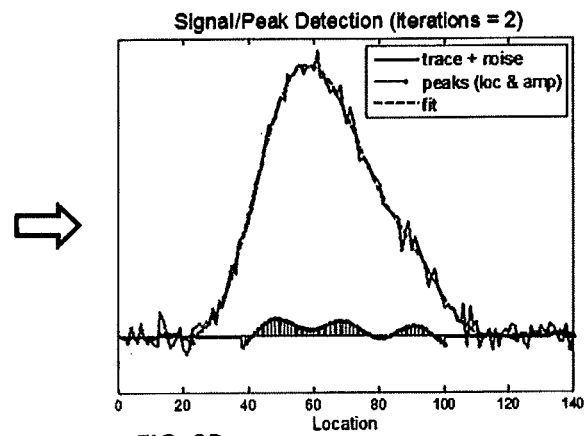
FIG. 9B
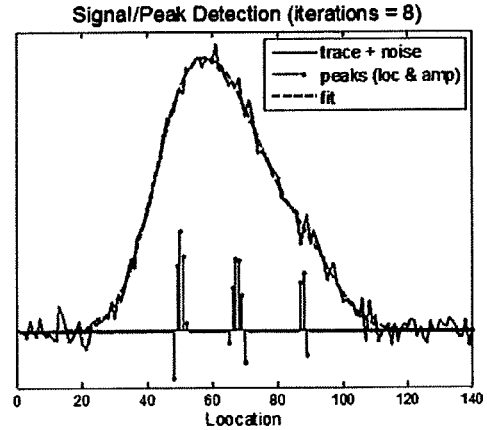
FIG. 9C
FIG. 9E
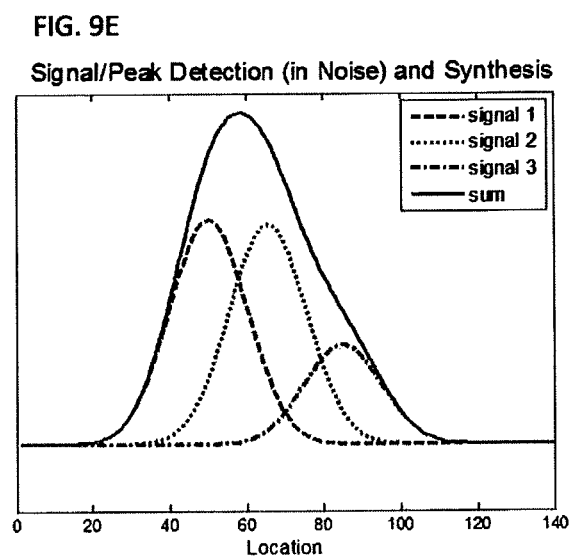
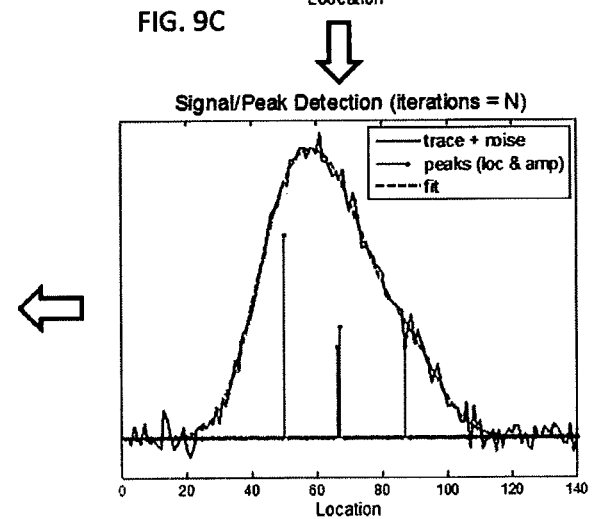
FIG. 9D

ADAPTIVE ASYMMETRICAL SIGNAL DETECTION AND SYNTHESIS METHODS AND SYSTEMS

CROSS REFERENCES TO RELATED APPLICATIONS

This application is a continuation-in-part of U.S. Non-Provisional application Ser. No. 15/914,737, filed, which is a continuation-in-part of U.S. Non-Provisional application Ser. No. 15/185,983, filed Jun. 17, 2016, now U.S. Pat. No. 9,971,936, and claims priority to U.S. Provisional Application No. 62/533,430, filed Jul. 17, 2017, which are all incorporated herein by reference.

FEDERALLY SPONSORED RESEARCH OR DEVELOPMENT

This invention was made with Government support under Grant Number 1R43GM112289-04 awarded by the National Institutes of Health. The Government has certain rights in this invention.

BACKGROUND

The present disclosure relates to the field of computing, and in particular to methods and apparatus for analyzing and/or filtering any data stream of trace data or image data to determine constituent signals and displaying the constituent signals of the data stream. Examples of data streams include data streams with data representing still images, video, and other one-dimensional, two-dimensional, three-dimensional, four-dimensional, and higher-dimensional data sets.

BRIEF SUMMARY

The present disclosure provides systems and methods for detecting, decoupling and quantifying unresolved signals in trace signal data in the presence of noise with no prior knowledge of the signal characteristics (e.g., signal peak location, intensity and width) of the unresolved signals other than the general expected shape of the signal(s) (e.g., generalized signal model function such as Gaussian or skewed Gaussian). The systems and methods are useful for analyzing any trace data signals having one or multiple overlapping constituent signals and particularly useful for analyzing electrophoresis data signals, chromatography data signals, spectroscopy data signals, and like data signals which often contain an unknown number of constituent signals with varying signal characteristics, such as peak location, peak intensity and peak width, and varying resolutions. The systems and methods are useful for analyzing any trace data signals having constituent signal(s) with unknown levels of asymmetry (skew).

According to an embodiment, a processor-implemented method is provided for processing a trace signal to determine two or more overlapping signal components of the trace signal. The method typically includes receiving trace signal data, the trace signal data including a plurality N of data points and representing at least M signals within a bandwidth defining the trace data, wherein M is an integer greater than or equal to 1, and processing the trace signal data, separately for each of a plurality of test signal width values, to produce spectral response data including a signal location and a signal intensity value for each of one or more detected signal components of the trace signal data for each of the plurality of test signal width values. The method also typically includes for each of the plurality of test signal width values, determining one or more detected signal component groups in the spectral response data based on the signal intensity values of the one or more detected signal components, each detected signal component group comprising one or more of the detected signal components corresponding to one or more consecutive signal locations having a non-zero, positive signal intensity value, and determining one or more signal characterization parameters for each of the one or more detected signal component groups, wherein the one or more signal characterization parameters includes at least a location of each of the one or more detected signal component groups, and wherein the location of each of the one or more detected signal component groups is determined by calculating a centroid of the locations of the one or more detected signal components making up the detected signal component group. The method further typically includes thereafter performing an iterative combinatorial optimization process on all or a subset of the detected signal component groups determined for all or a subset of the test signal width values, based on one or more of the signal characterization parameters of the one or more detected signal component groups, to determine a final set of one or more detected signal component groups having a best match relative to the trace signal data, and outputting locations, intensities and signal widths of one or more signal components of the trace signal data based on the final set of one or more detected signal component groups.

In certain aspects, performing the iterative combinatorial optimization process includes selecting an initial set of one or more detected signal component groups, and at each iteration: i) determining a composite signal comprising the initial set of one or more detected signal component groups; ii) determining a percent fit error for the composite signal relative to the trace signal data; iii) selecting an unused detected signal component group, wherein the unused detected signal component group is a detected signal component group that has not been included in the initial set of one or more detected signal component groups during any iteration; iv) adding the unused detected signal component group to the initial set or replacing one of the detected signal component groups in the initial set with the unused detected signal component group to form an altered set of one or more detected signal component groups; and v) determining the final set of one or more detected signal component groups by iteratively repeating steps i) through iv) using the altered set of one or more detected signal component groups as the initial set of one or more detected signal component groups until all detected signal component groups in the all or the subset of the detected signal component groups has been used in at least one iteration of step iv), wherein the final set corresponds to the altered set having the best match as determined in step ii).

In certain aspects, processing the trace signal data to produce the spectral response data for a specified test signal width value includes defining an initial set of signal components to be the number N of data points, wherein initial signal locations for each of the signal components of the initial set of signal components correspond to the locations within the bandwidth of the number N of data points. The method also typically includes a) simultaneously performing a numerical method signal extraction calculation on each signal component in the initial set of signal components, b) determining a signal amplitude value for each signal component of the initial set of signal components based on the extraction calculation, c) removing from the initial set of signal components, or attenuating, each signal component determined to have a negative signal amplitude value based on the extraction calculation to produce an adjusted set of signal components, and d) determining a final set of signal components by iteratively repeating steps a)-c) using the adjusted set of signal components as the initial set of signal components until no signal component has a negative amplitude value based on the extraction calculation.

In certain aspects, the signal characterization parameters further include, for each of the one or more detected signal component groups, a signal detection width value, amplitude and error value, and a differential error value. In certain aspects, the determining the one or more signal characterization parameters for each of the one or more detected signal component groups further includes determining the signal detection width value for each of the one or more detected signal component groups by calculating a combined width of the one or more detected signal components making up the detected signal component group, determining the amplitude of each of the one or more detected signal component groups by calculating a summation of the intensity values of the one or more detected signal components making up the detected signal component group, calculating the error value for each of the one or more detected signal component groups, and calculating the differential error value for each of the one or more detected signal component groups.

According to an embodiment, a processor-implemented method of processing a trace signal to determine one or more unknown signal components of the trace signal is provided. The method typically includes receiving trace signal data, the trace signal data including a plurality N of data points and representing at least M signals within a bandwidth defining the trace data, wherein M is an integer greater than or equal to 1, and defining an initial set of signal components to be the number N of data points, wherein initial signal locations for each of the signal components of the initial set of signal components correspond to the locations within the bandwidth of the number N of data points. The method also typically includes a) simultaneously performing a numerical method signal extraction calculation on each signal component in the initial set of signal components, b) determining a signal amplitude value for each signal component of the initial set of signal components based on the extraction calculation, c) removing from the initial set of signal components, or attenuating, each signal component determined to have a negative signal amplitude value based on the extraction calculation to produce an adjusted set of signal components, and d) determining a final set of signal components by iteratively repeating steps a)-c) using the adjusted set of signal components as the initial set of signal components until no signal component has a negative amplitude value based on the extraction calculation. The method further typically includes outputting signal locations and signal intensities of one or more signal components of the trace signal based on the final set of signal components. The output signal locations and intensities may be displayed on a display and/or further processed to determine additional information.

In certain aspects, outputting signal locations and signal intensities of the one or more signal components of the trace signal based on the final set of signal components includes identifying one or more amplitude groups in the final set of signal components, each amplitude group comprising signal components corresponding to one or more consecutive locations each having a non-zero, positive amplitude value, determining a signal location for each of the one or more signal components of the trace signal by calculating a centroid of the corresponding amplitude group, and determining a signal intensity for each of the one or more signal components of the trace signal by summing the amplitude values of the signal components within the corresponding amplitude group.

In certain aspects, all or a subset of the signal components in the trace data are assumed to have the same curve profile type when performing the numerical method signal extraction calculation, wherein the curve profile type is selected from the group consisting of a Gaussian profile, a bi-Gaussian profile, an exponentially modified Gaussian profile, a Haarhoff-van der Linde profile, a Lorentzian profile or a Voigt profile. In certain aspects, the numerical method extraction calculation includes a conjugate gradient method, a Generalized Minimum Residual method, a Newton's method, a Broyden's method or a Gaussian elimination method. In certain aspects, the numerical method signal extraction calculation is performed using a matrix formulation, wherein determining a signal amplitude value includes identifying indices of an amplitude matrix that have negative amplitudes, and wherein removing or attenuating includes updating a weighting matrix so that weight values of the corresponding identified indices in the weighting matrix are each multiplied by an attenuation factor, wherein the attenuation factor is less than 1 and greater than or equal to zero.

According to yet another embodiment, a processor-implemented method of processing a trace signal to determine one or more unknown signal components of the trace signal is provided, wherein the one or more unknown signal components having the same or dissimilar signal widths and the same or different asymmetry. The method typically includes receiving trace signal data, the trace signal data including a plurality N of data points and representing at least M signals within a bandwidth defining the trace data, wherein M is an integer greater than or equal to 1, and for each of a plurality of asymmetry values: a) processing the trace signal data, separately for each of a plurality of test signal width values, to produce spectral response data including a signal location value and a signal intensity value for each of one or more detected signal components of the trace signal data for each of the plurality of test signal width values, wherein each test signal width value is a function of the asymmetry value; b) for each of the plurality of test signal width values: i) determining one or more detected signal component groups in the spectral response data based on the signal intensity values of the one or more detected signal components, each detected signal component group comprising one or more of the detected signal components corresponding to one or more consecutive signal locations having a non-zero, positive signal intensity value, and ii) determining one or more signal characterization parameters for each of the one or more detected signal component groups, wherein the one or more signal characterization parameters includes at least a location of each of the one or more detected signal component groups, and wherein the location of each of the one or more detected signal component groups is determined by calculating a centroid of the locations of the one or more detected signal components making up the detected signal component group, and thereafter c) performing an iterative combinatorial optimization process on all or a subset of the detected signal component groups determined for all test signal width values, based on one or more of the signal characterization parameters of the one or more detected signal component groups, to determine a final set of one or more detected signal component groups having a best match relative to the trace signal data. The method also typically includes determining, from among all the final sets of one or more detected signal component groups, an optimal final set that produces the lowest percent fit error relative to the trace signal data, and outputting locations, intensities and signal widths of one or more signal components of the trace signal data based on the optimal final set of one or more detected signal component groups.

In certain aspects, a test width value includes a first test width value, $\sigma_1$, defining a width to a left side of the signal location value and a second test width value, $\sigma_2$, defining a width to the right of the signal location value. In certain aspects, $$\sigma_1 = \sigma\left(\frac{2s}{(s+1)}\right), \quad \sigma_2 = \sigma\left(\frac{2}{(s+1)}\right),$$

and wherein s is the asymmetry value. In certain aspects, the plurality of asymmetry values include a minimum specified value and a maximum specified value, and wherein each of the plurality of asymmetry values is proportionally spaced within a range defined by the minimum specified value and the maximum specified value.

According to another embodiment, a non-transitory computer readable medium storing code, which when executed by one or more processors cause the one or more processors to implement a method of processing a trace signal to determine one or more unknown signal components of the trace signal, the code including instructions to perform various steps as mentioned above, and herein below.

According to yet another embodiment, a processing device is provided that processes a trace signal to determine one or more unknown signal components of the trace signal according to some or all of the various method steps as mentioned above, and herein below. The device typically includes a processor, and a memory storing code executable by the processor, wherein the code includes instructions, which, when executed by the processor, cause the processor to perform various steps as mentioned above, and herein below.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE SEVERAL VIEWS OF THE DRAWING(S)

The detailed description is described with reference to the accompanying figures. The use of the same reference numbers in different instances in the description and the figures may indicate similar or identical items.

Figure 7:
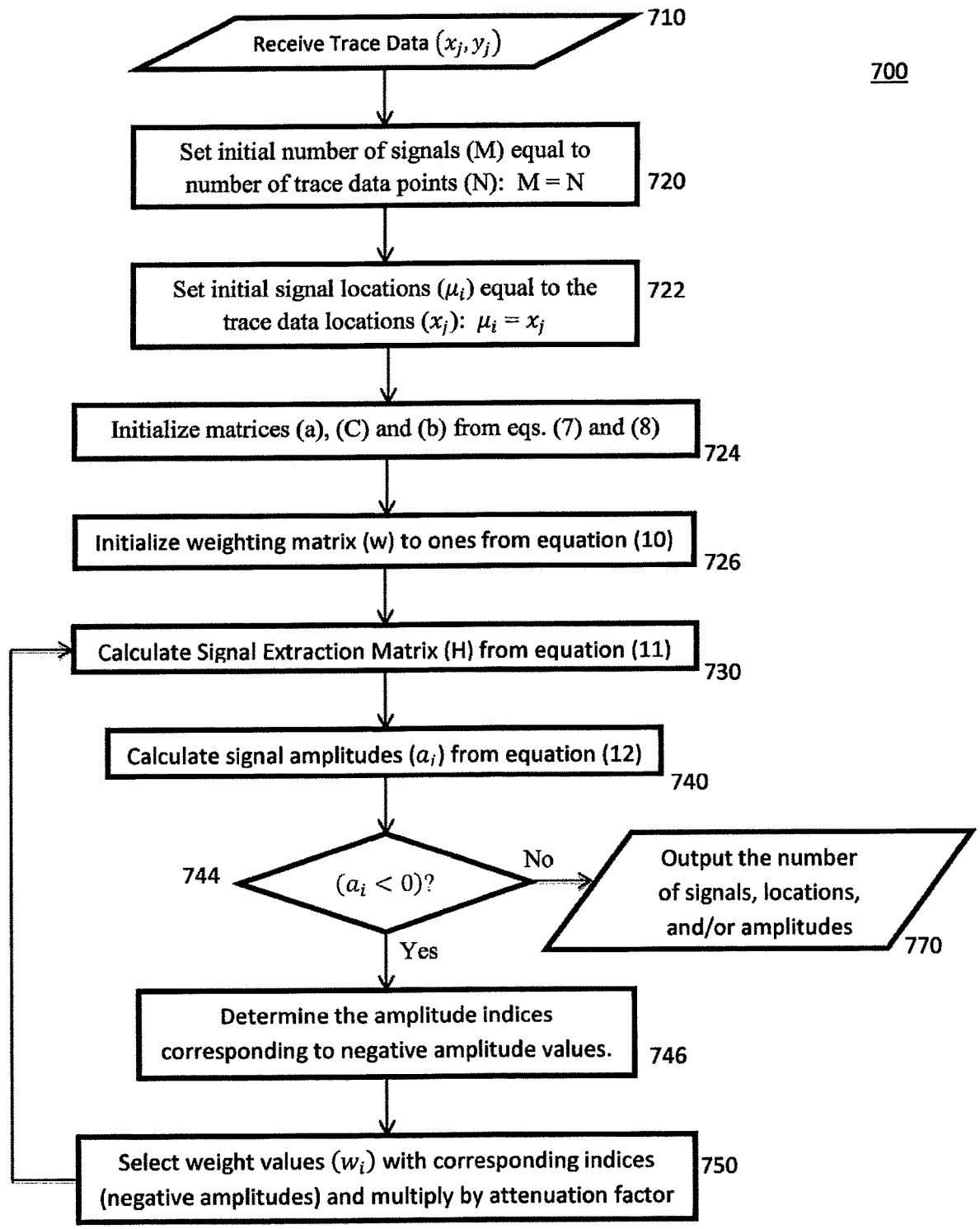
FIG. 7 is a flow diagram of a matrix formulation of a signal detection and synthesis method (Phase I) according to an embodiment.

FIGS. 8A-8E illustrate examples of processing a trace signal without noise according to the method of FIG. 7: FIG. 8A shows the original trace signal data; FIG. 8B shows the reduced set of trial signals after two processing iterations; FIG. 8C shows the reduced set of trial signals after eight processing iterations; FIG. 8D shows the reduced set of trial signals after N processing iterations; FIG. 8E shows a visual representation of the three constituent signals and their determined characteristics and a visualization of the sum of the three constituent signals, which matches the original trace signal data shown in FIG. 8A.

FIGS. 9A-9E illustrate examples of processing a trace signal with noise according to the method of FIG. 7: FIG. 9A shows the original trace signal data; FIG. 9B shows the reduced set of trial signals after two processing iterations; FIG. 9C shows the reduced set of trial signals after eight processing iterations; FIG. 9D shows the reduced set of trial signals after N processing iterations; FIG. 9E shows a visual representation of the three constituent signals and their determined characteristics and a visualization of the sum of the three constituent signals, which substantially matches the original trace signal data shown in FIG. 9A.

Figure 10:
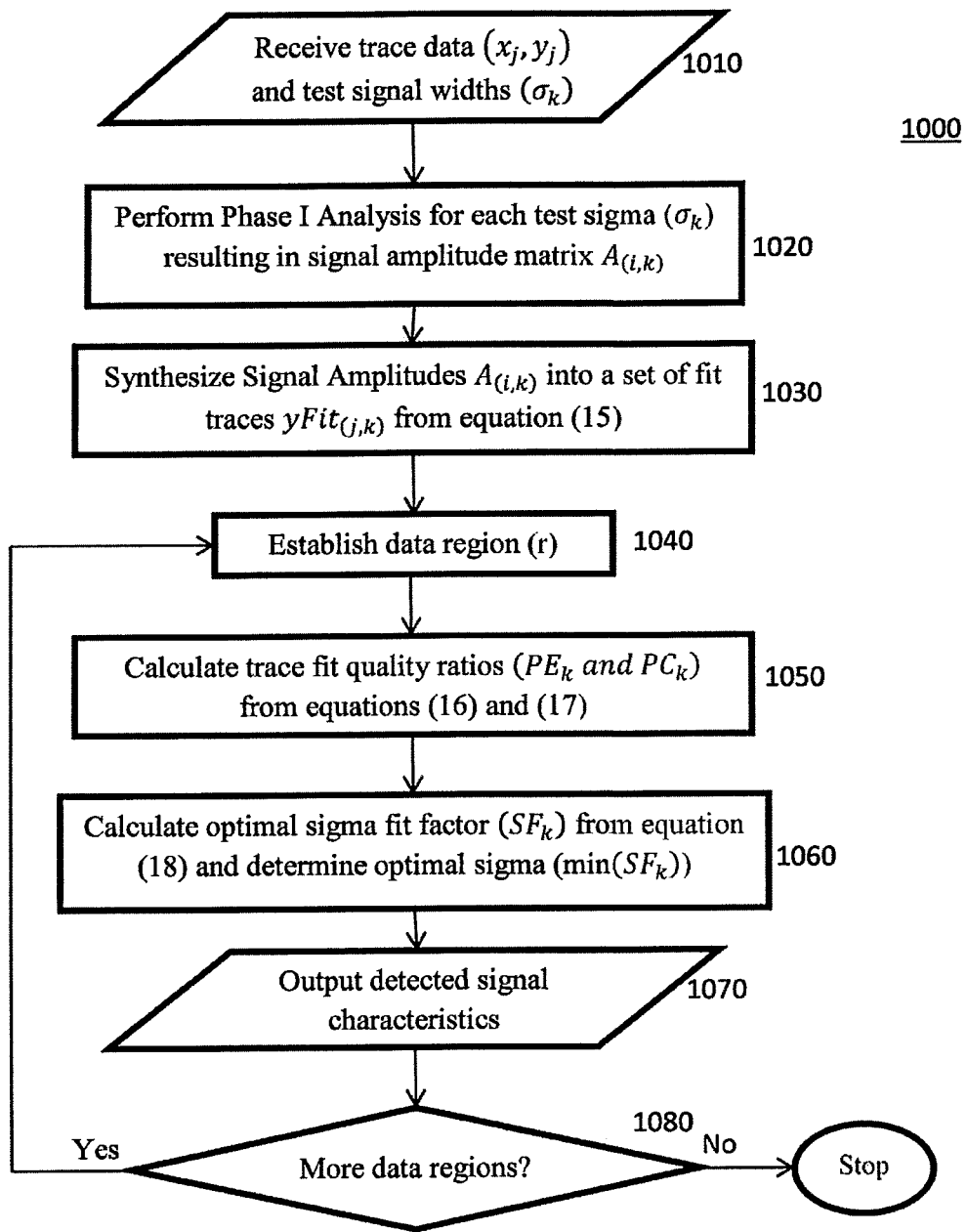

FIG. 10 is a flow diagram of a matrix formulation of a signal width (sigma) determination method (Phase II) according to an embodiment.

Figure 11A:
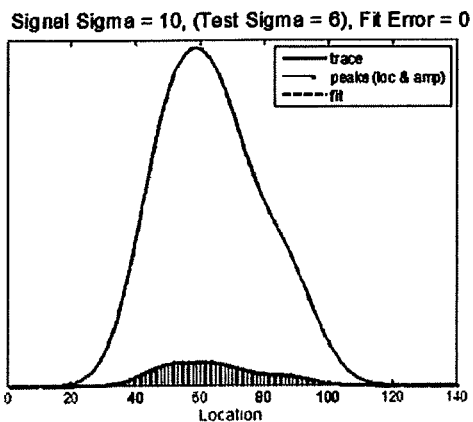
Figure 11B:
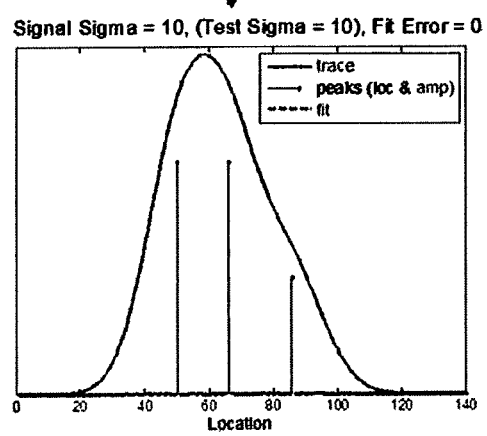
Figure 11C:
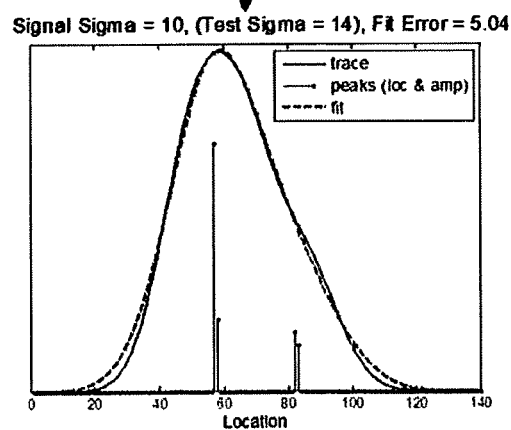

FIGS. 11A-11C illustrate example Phase II results for trace signal data without noise, where the true signal width (sigma) is 10: FIG. 11A shows results for a test sigma of 6 with a fit error of 0; FIG. 11B shows results for a test sigma of 10 with a fit error of 0; and FIG. 11C shows results for a test sigma of 14 with a fit error of 5.04.

Figure 12:
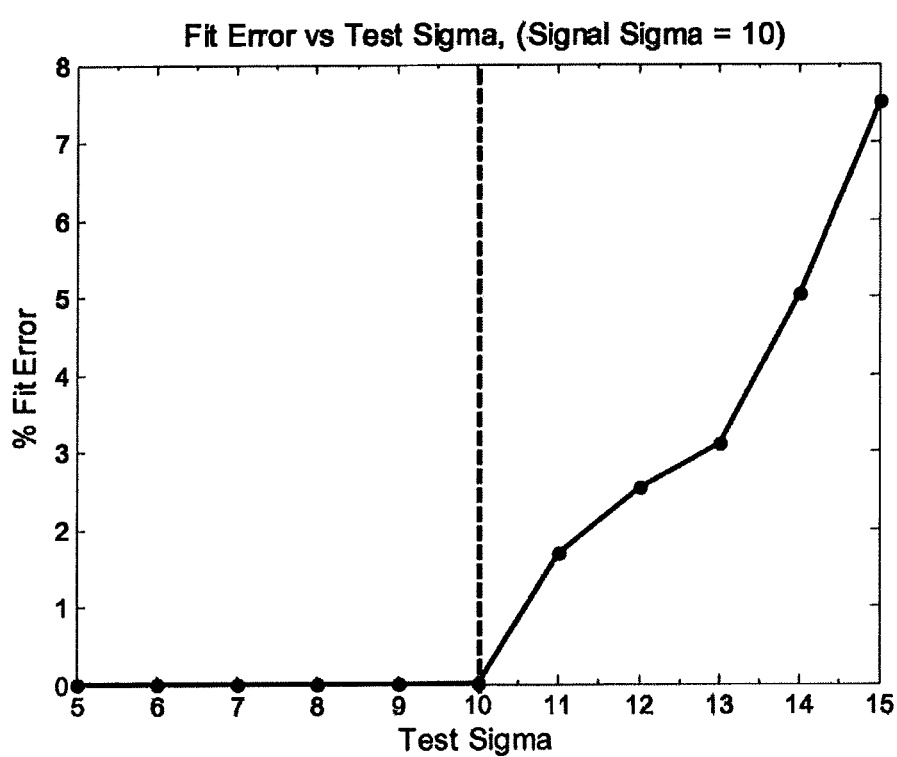

FIG. 12 illustrates a graph of fit error (or $PE_k$) vs. test sigma.

Figure 13:
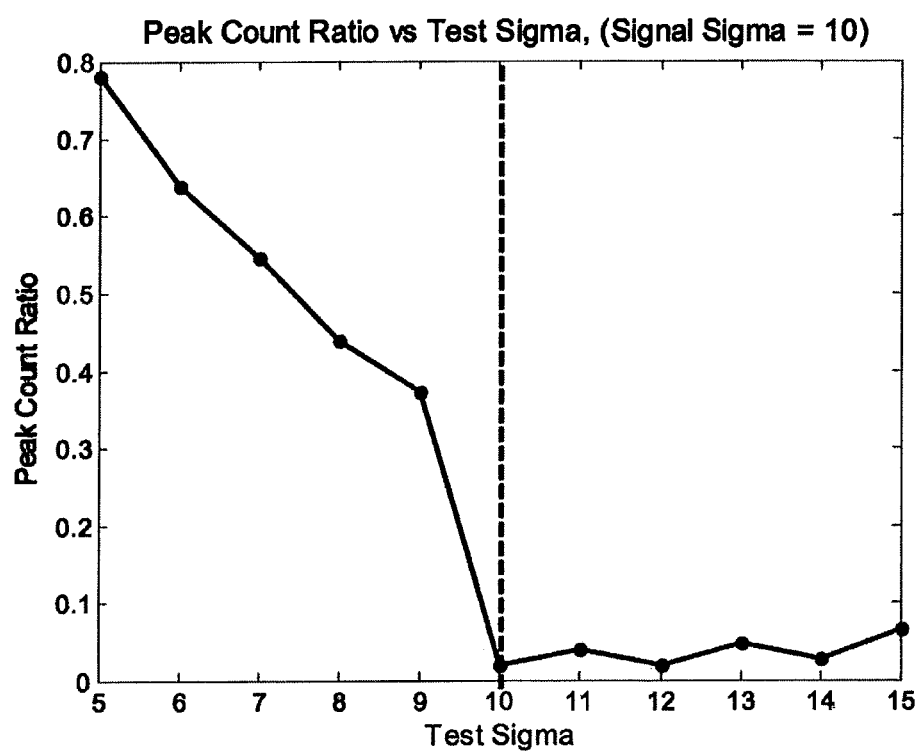

FIG. 13 illustrates a graph of peak count ratio (or $PC_k$) vs. test sigma.

Figure 14:
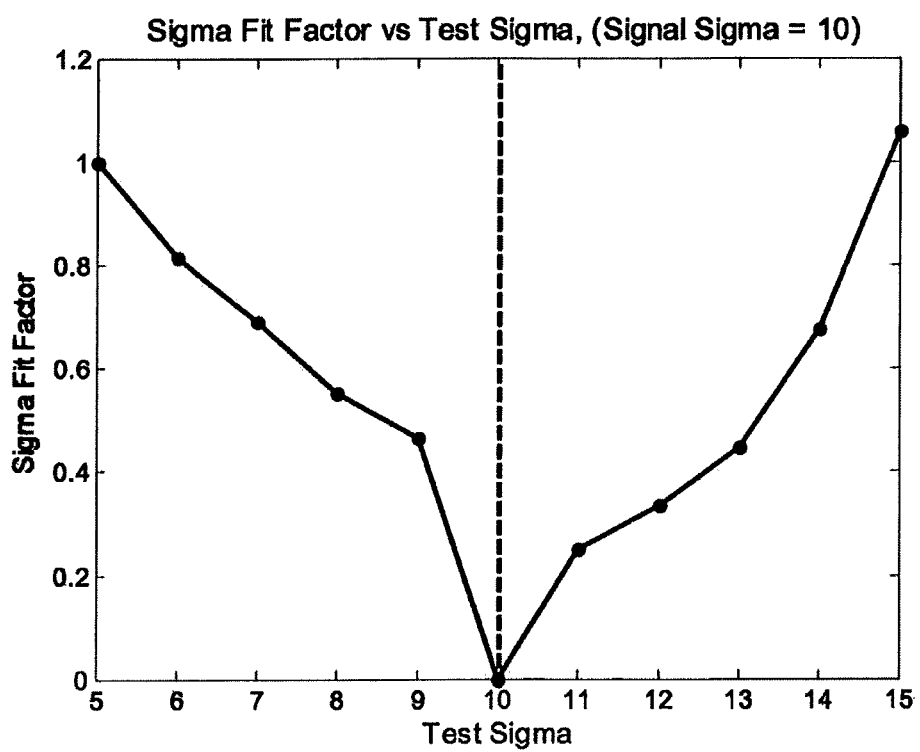

FIG. 14 illustrates a graph of calculated sigma fit factor (or $SF_k$) vs. test sigma.

Figure 15A:
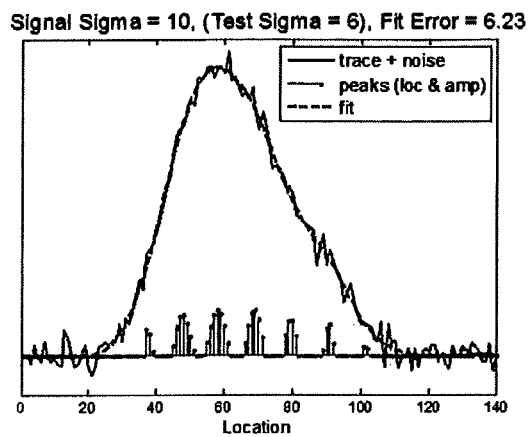
Figure 15B:
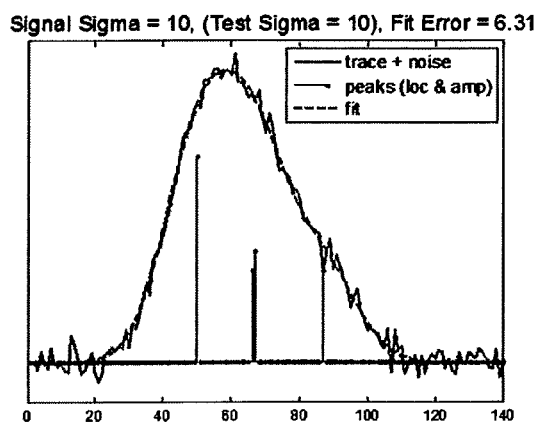
Figure 15C:
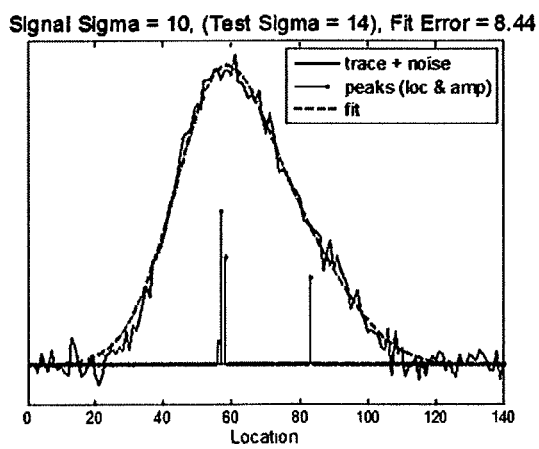

FIGS. 15A-15C illustrates example Phase II results for trace signal data in the presence of noise, where the true signal width (sigma) is 10: FIG. 15A shows results for a test sigma of 6 with a fit error of 6.23; FIG. 15B shows results for a test sigma of 10 with a fit error of 6.31; and FIG. 15C shows results for a test sigma of 14 with a fit error of 8.44.

Figure 16:
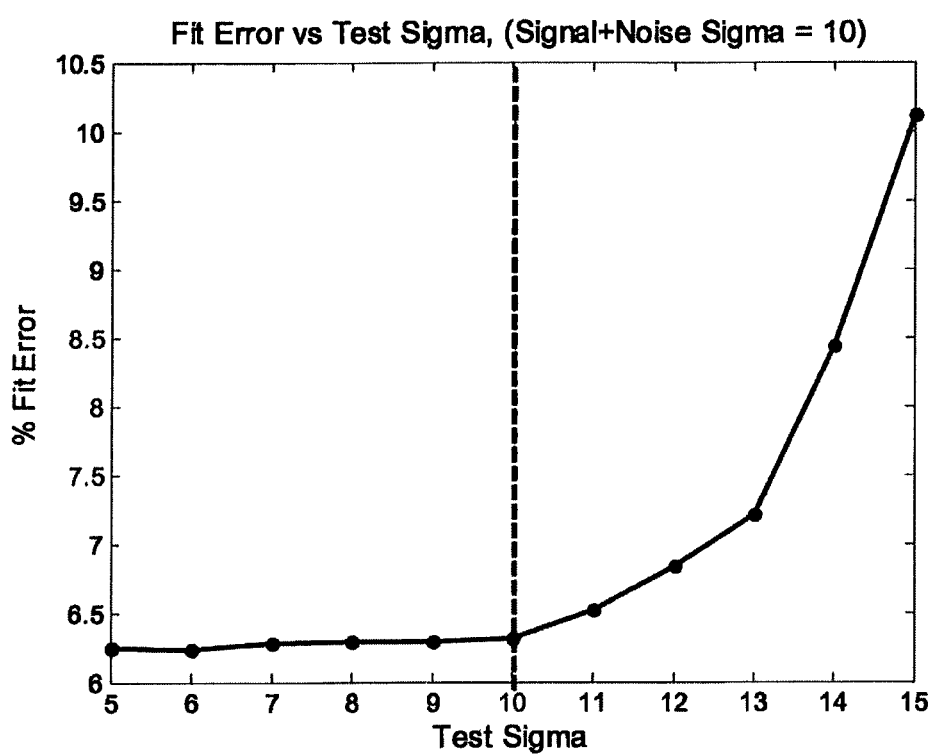

FIG. 16 illustrates a graph of fit error (or $PE_k$) vs. test sigma.

Figure 17:
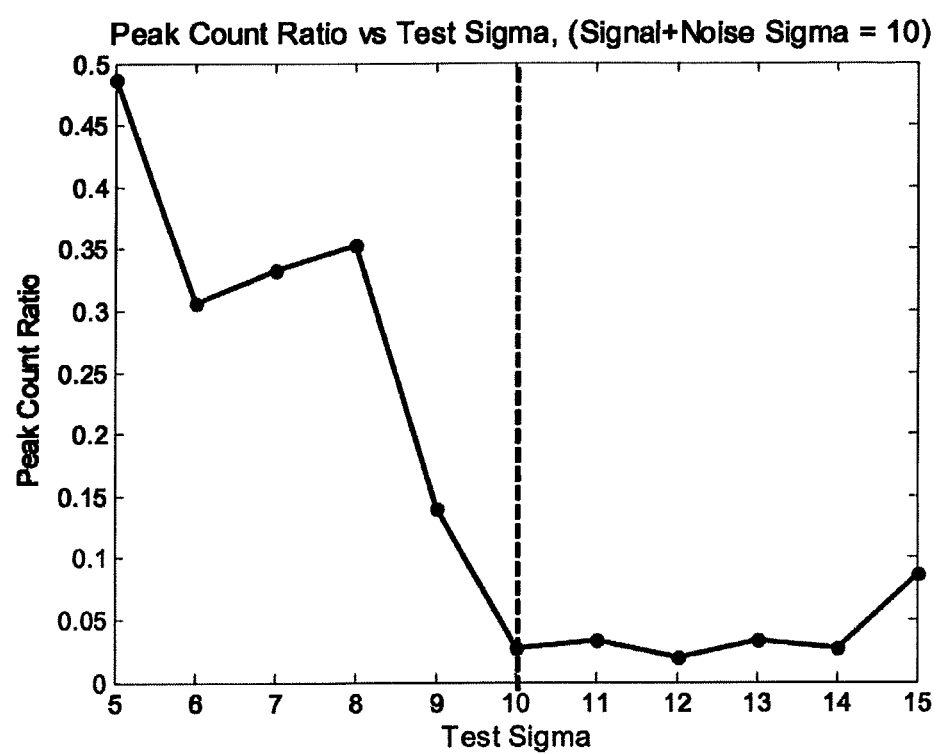

FIG. 17 illustrates a graph of peak count ratio (or $PC_k$) vs. test sigma.

Figure 18:
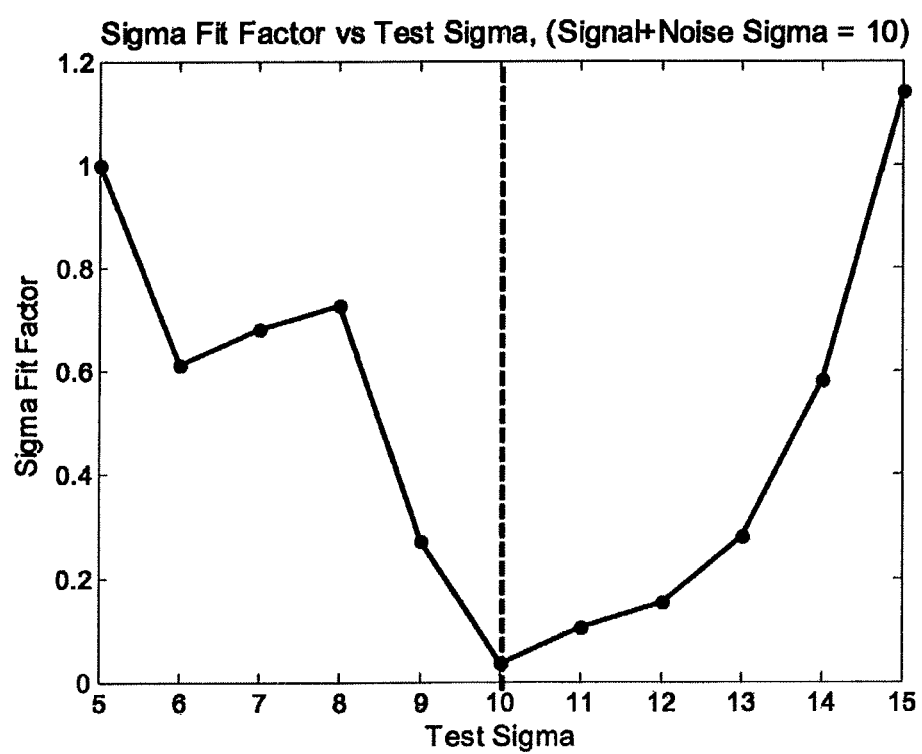

FIG. 18 illustrates a graph of calculated sigma fit factor (or $SF_k$) vs. test sigma.

Figure 19:
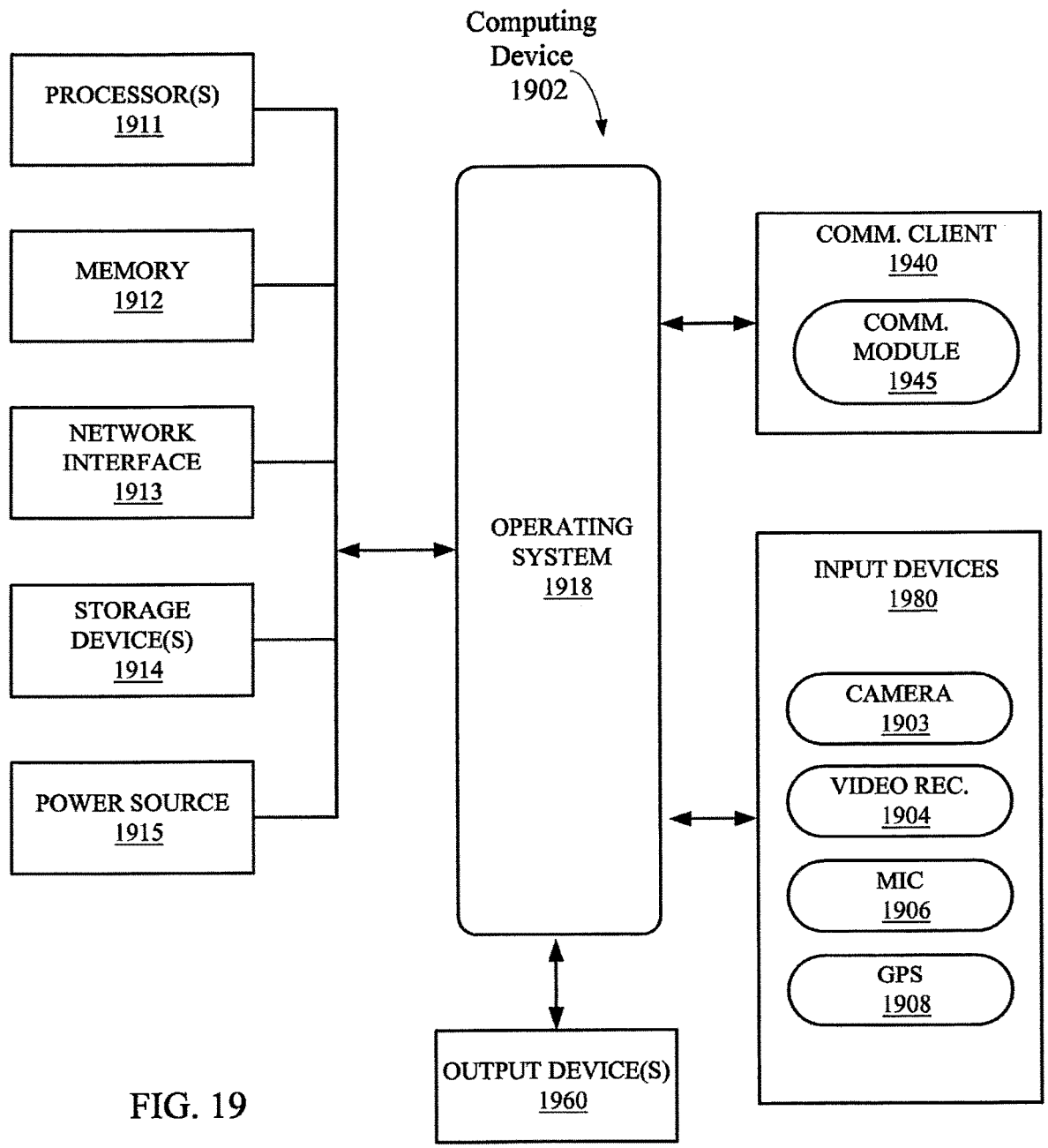

FIG. 19 is a block diagram of example functional components for a computing system or device configured to perform one or more of the analysis techniques described herein, according to an embodiment.

Figure 20:
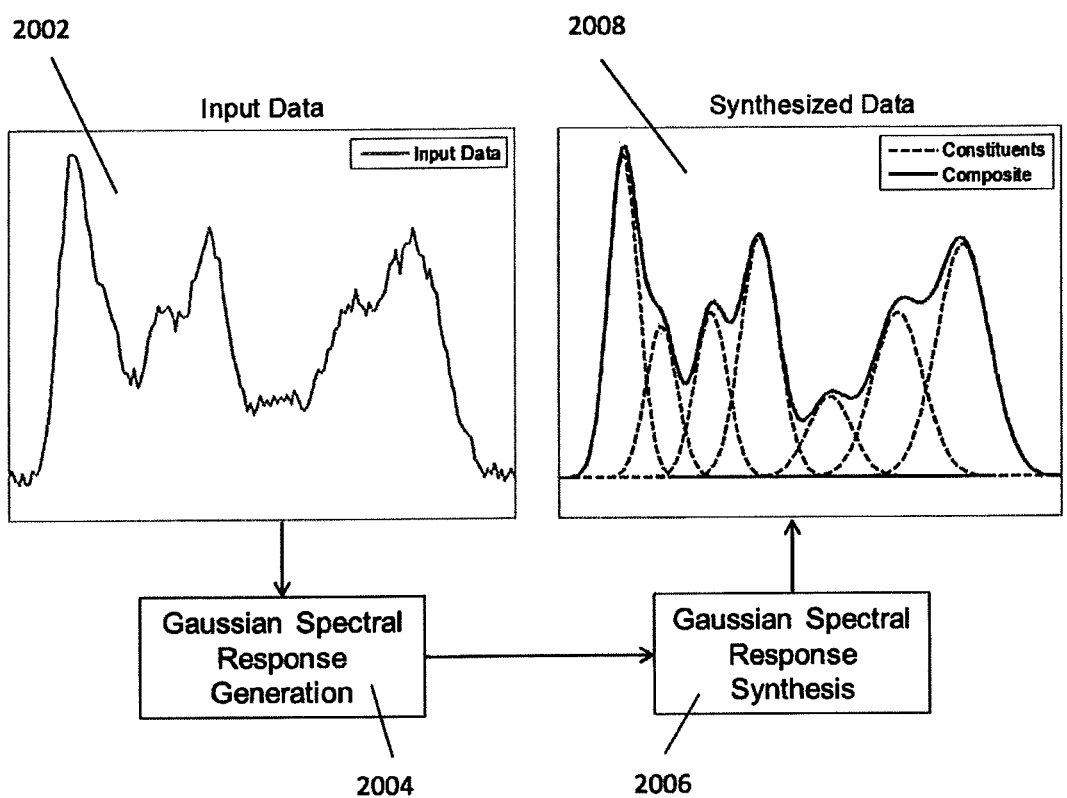

FIG. 20 illustrates a block diagram of an exemplary system for determining constituent signals having the same or dissimilar widths in trace signal data.

Figure 21:
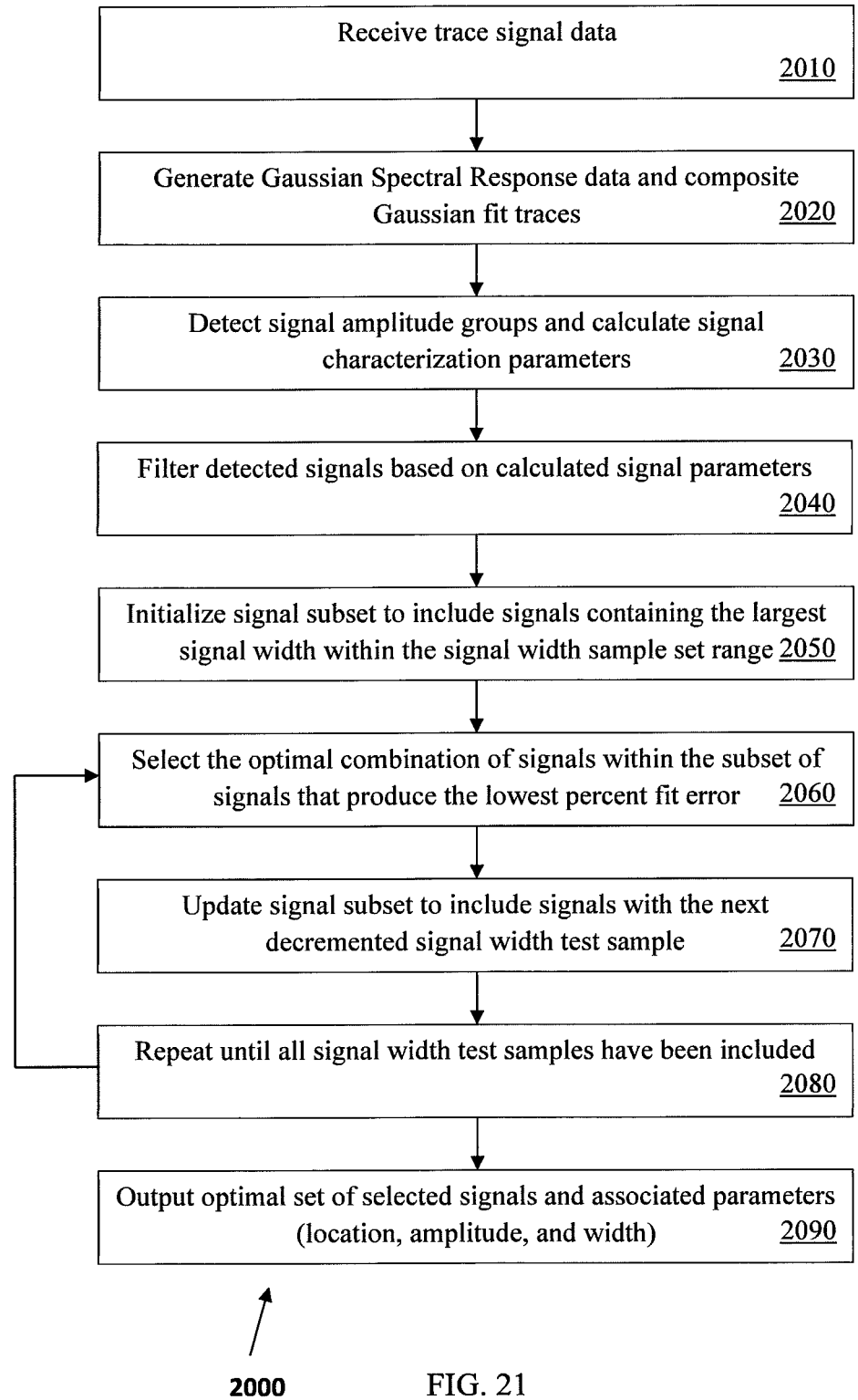

FIG. 21 is a flow diagram for a method of determining the number, location, intensity (i.e., amplitude), and width of each of one or more constituent signal present in trace signal data according to an embodiment.

Figure 22:
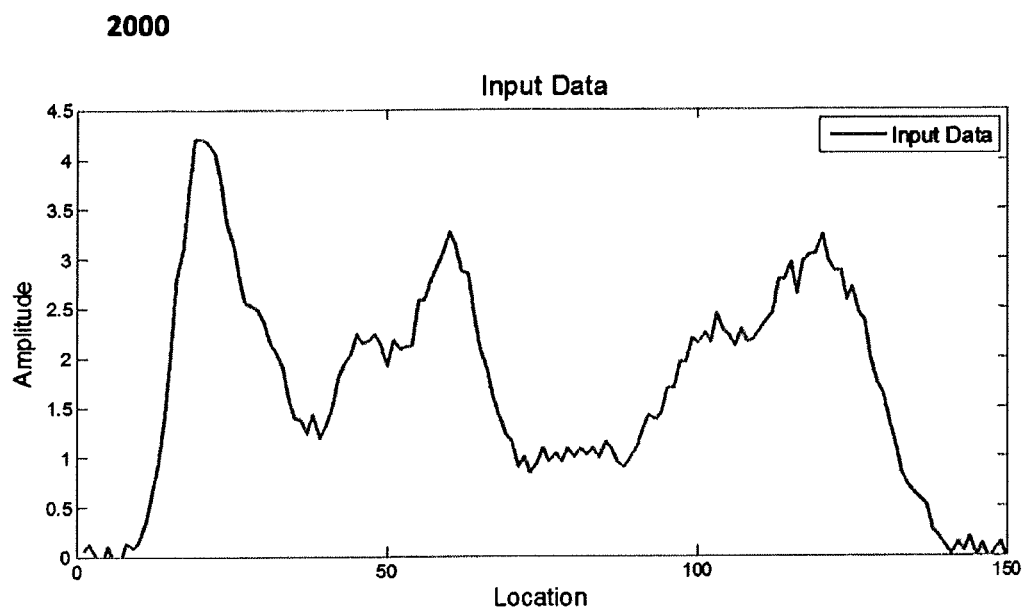

FIG. 22 illustrates an example of input trace signal data.

FIGS. 23-31 show example Gaussian Spectral Response data sets (e.g., stem plot, location and amplitude) and composite Gaussian fit traces for each of an initial set of nine (9) test signal width values.

Figure 32:
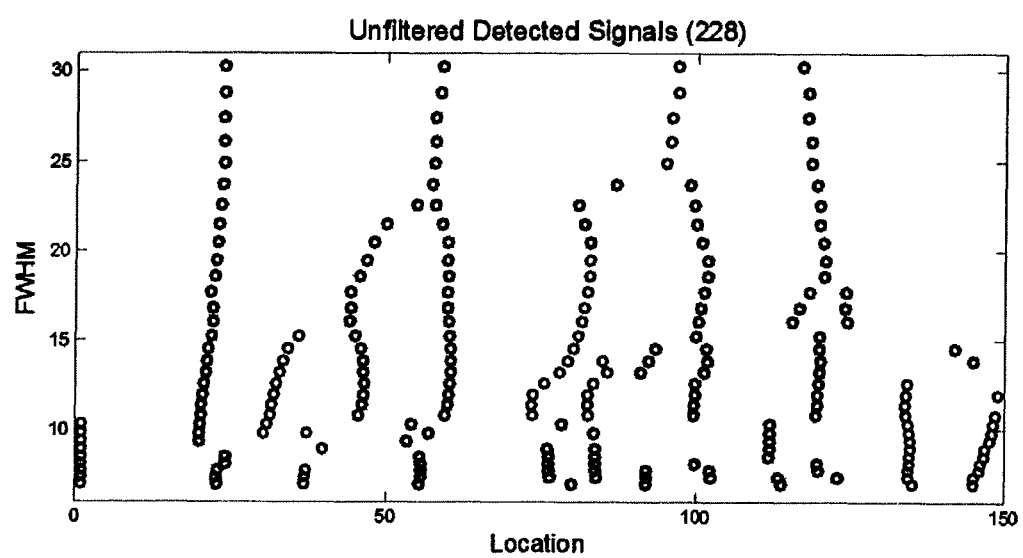

FIG. 32 illustrates an example of a scatter plot of all the (unfiltered) detected signal component groups, with the x-axis representing location and the y-axis representing the test signal width (e.g., FWHM).

FIGS. 33-37 illustrate examples of scatter plots of filtered, detected signal component groups according to filters applied to the detected signal component groups shown in FIG. 32.

Figure 38A:
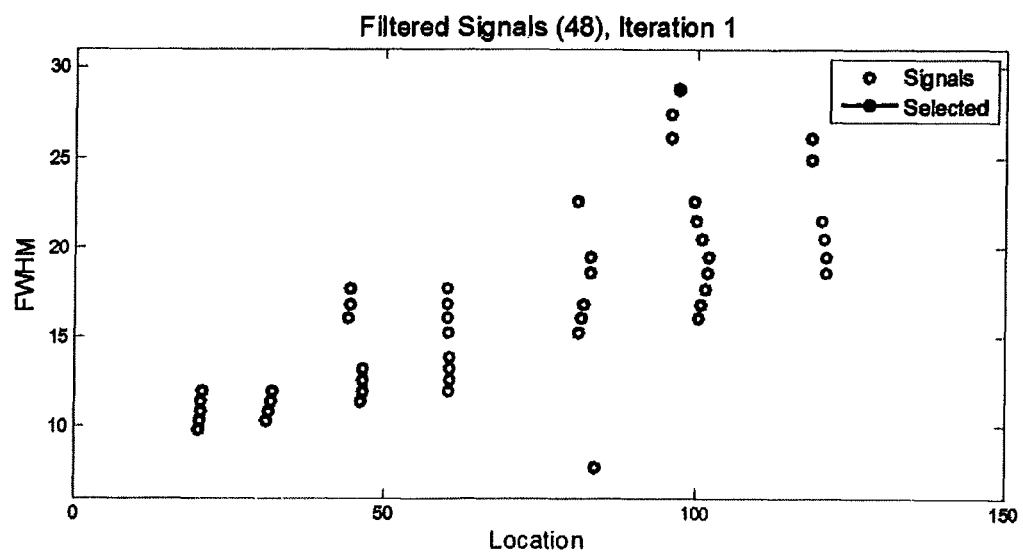

FIG. 38A shows a scatter plot that represents the selected signals from the first iteration (Iteration 1) of the selection process according to an embodiment.

Figure 38B:
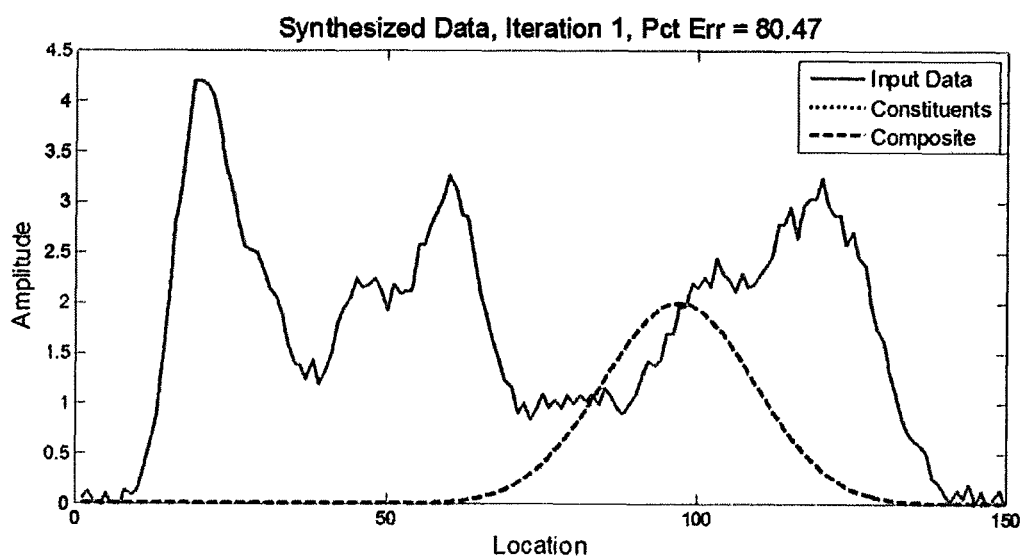

FIG. 38B shows synthesized data that represents the selected constituent signals, their composite, and the resultant percent error relative to the input trace from Iteration 1 according to an embodiment.

Figure 39A:
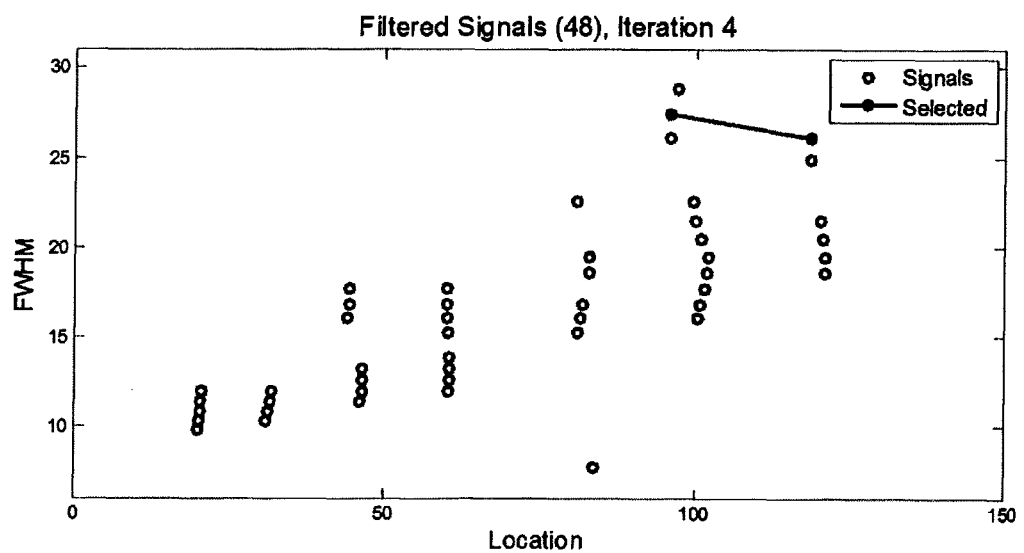

FIG. 39A shows a scatter plot that represents the selected signals from the fourth iteration (Iteration 4) of the selection process according to an embodiment.

Figure 39B:
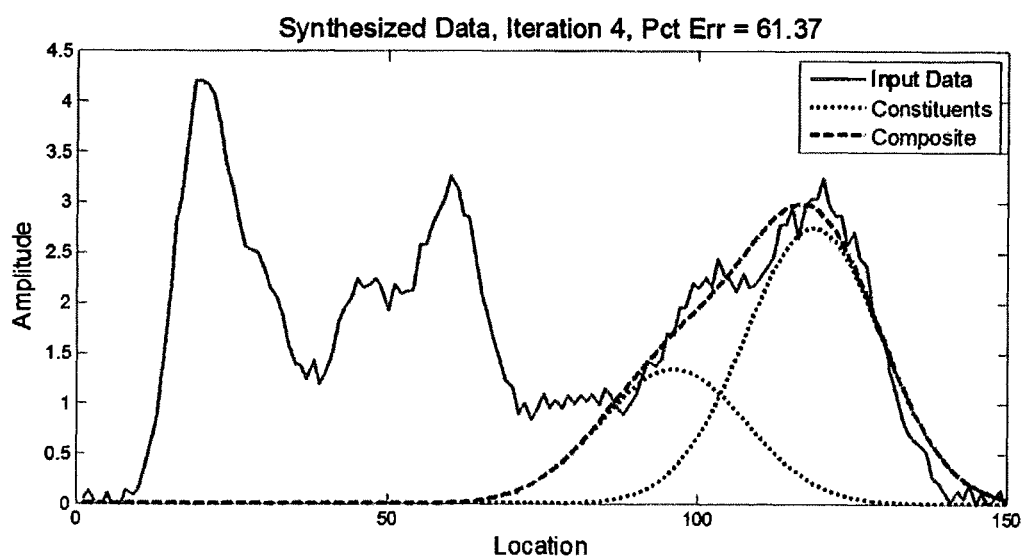

FIG. 39B shows synthesized data that represents the selected constituent signals, their composite, and the resultant percent error relative to the input trace from Iteration 4 according to an embodiment.

Figure 40A:
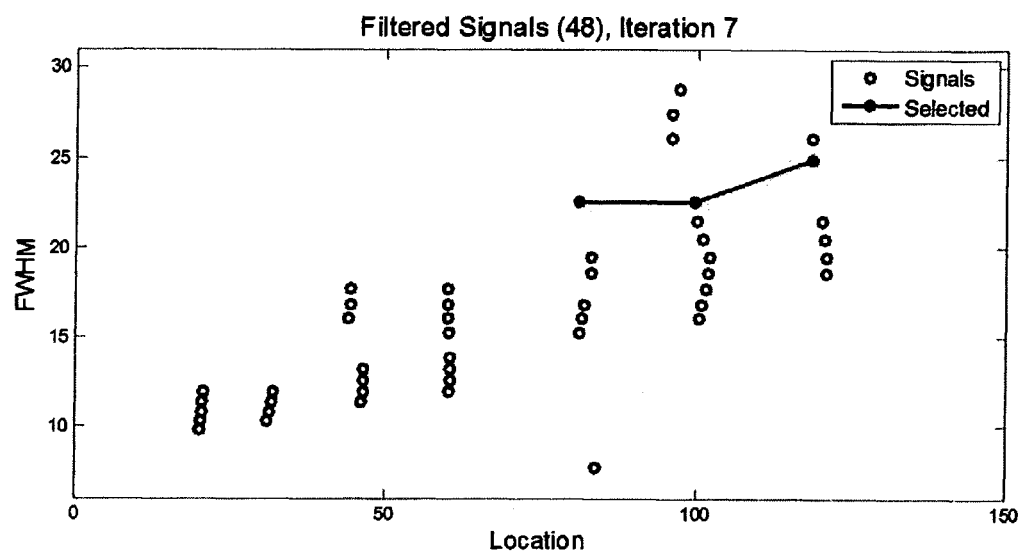

FIG. 40A shows a scatter plot that represents the selected signals from the seventh iteration (Iteration 7) of the selection process according to an embodiment.

Figure 40B:
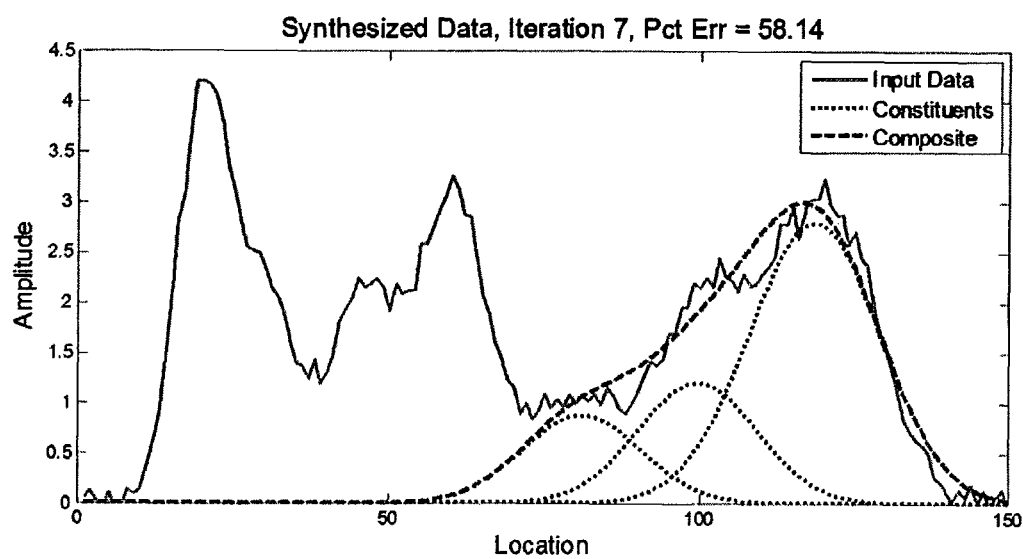

FIG. 40B shows synthesized data that represents the selected constituent signals, their composite, and the resultant percent error relative to the input trace from Iteration 7 according to an embodiment.

Figure 41A:
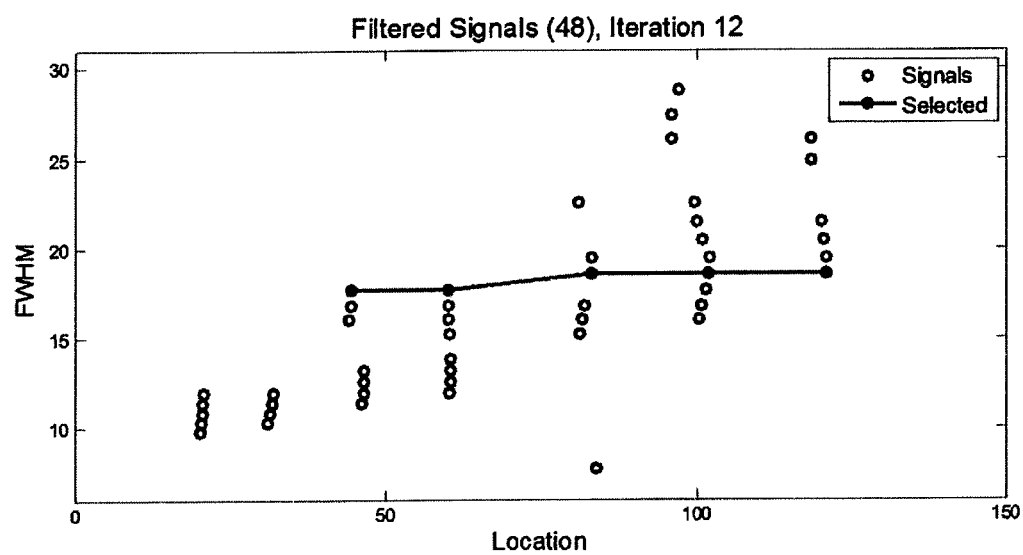

FIG. 41A shows a scatter plot that represents the selected signals from the twelfth iteration (Iteration 12) of the selection process according to an embodiment.

Figure 41B:
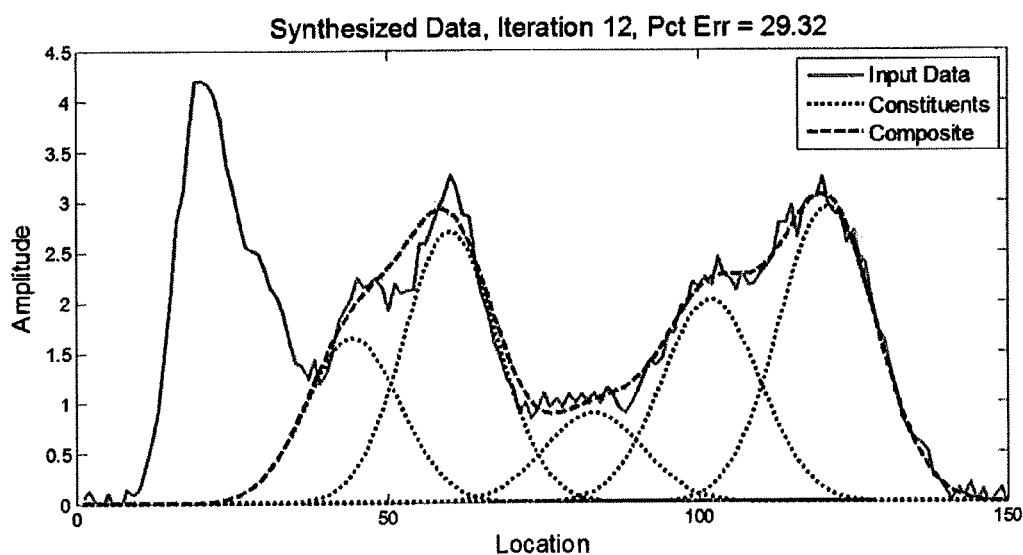

FIG. 41B shows synthesized data that represents the selected constituent signals, their composite, and the resultant percent error relative to the input trace from Iteration 12 according to an embodiment.

Figure 42A:
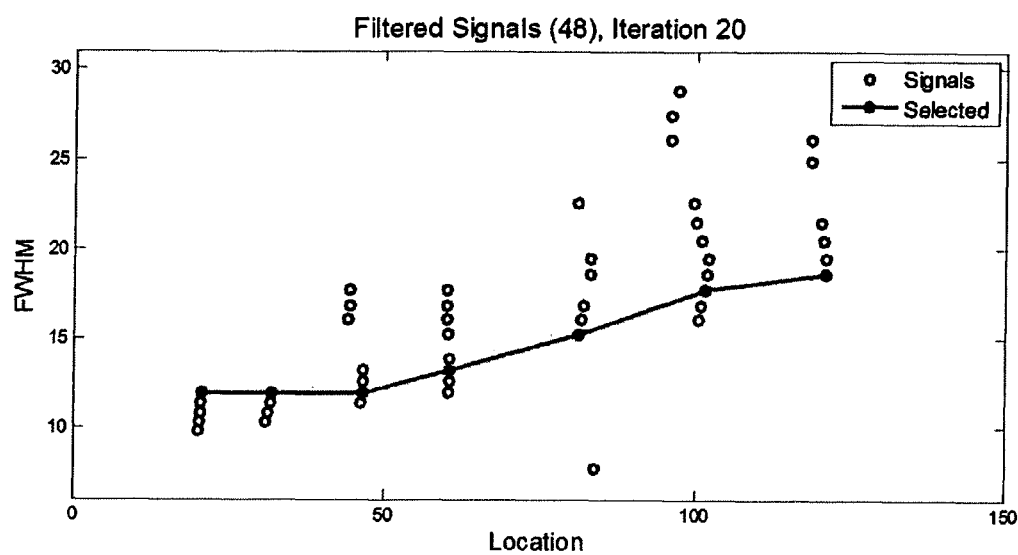

FIG. 42A shows a scatter plot that represents the selected signals from the twentieth iteration (Iteration 20) of the selection process according to an embodiment.

Figure 42B:
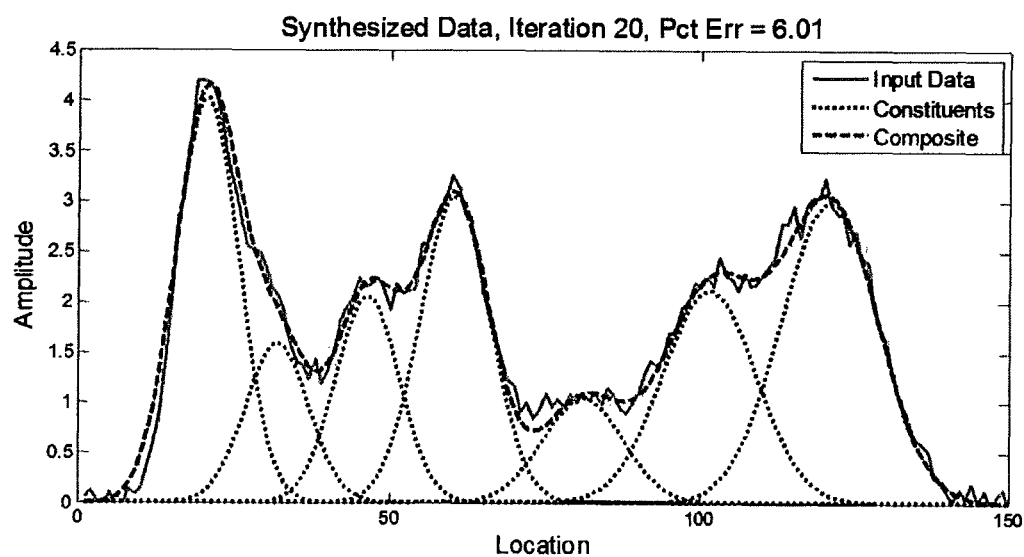

FIG. 42B shows synthesized data that represents the selected constituent signals, their composite, and the resultant percent error relative to the input trace from Iteration 20 according to an embodiment.

Figure 43A:
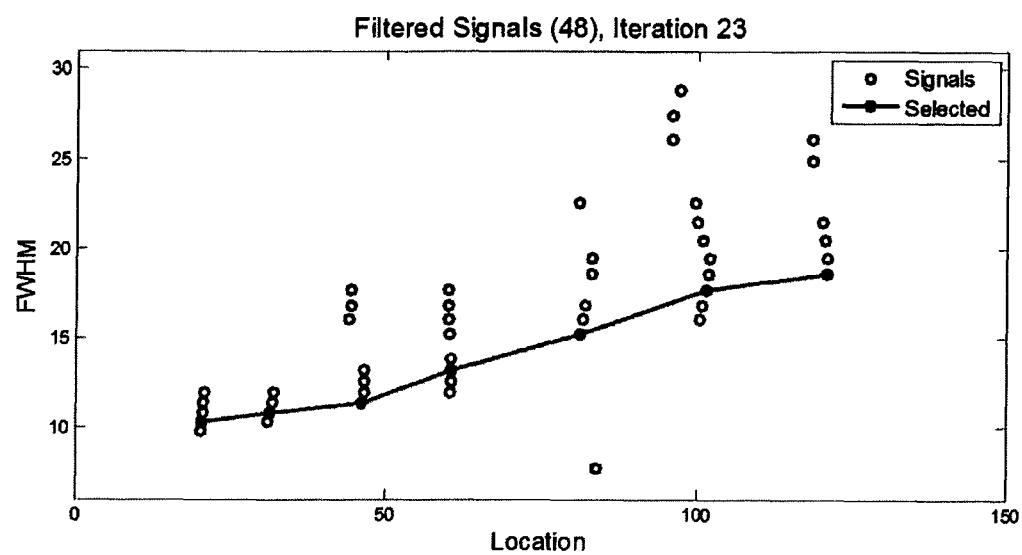

FIG. 43A shows a scatter plot that represents the selected signals from the twenty-third iteration (Iteration 23) of the selection process according to an embodiment.

Figure 43B:
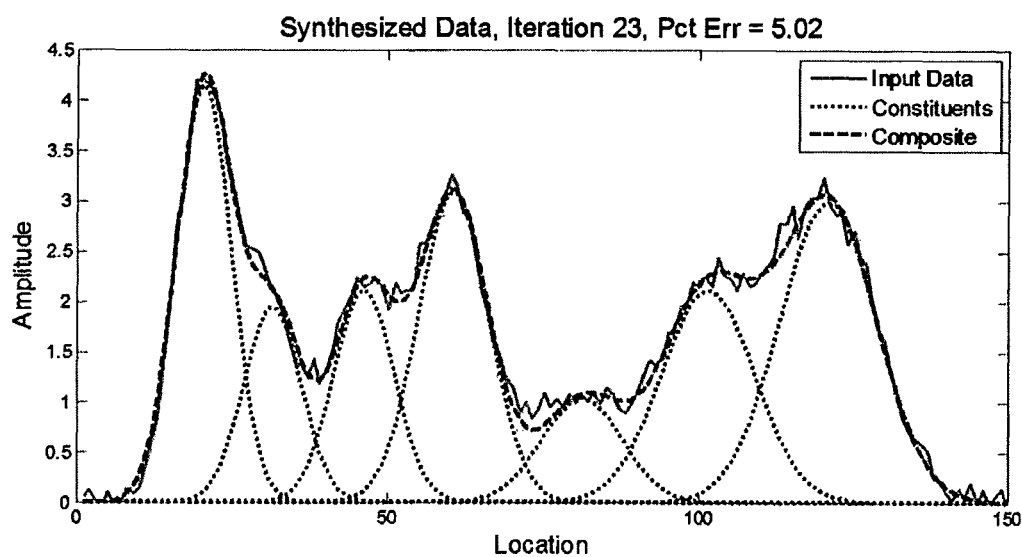

FIG. 43B shows synthesized data that represents the selected constituent signals, their composite, and the resultant percent error relative to the input trace from Iteration 23 according to an embodiment.

Figure 44:
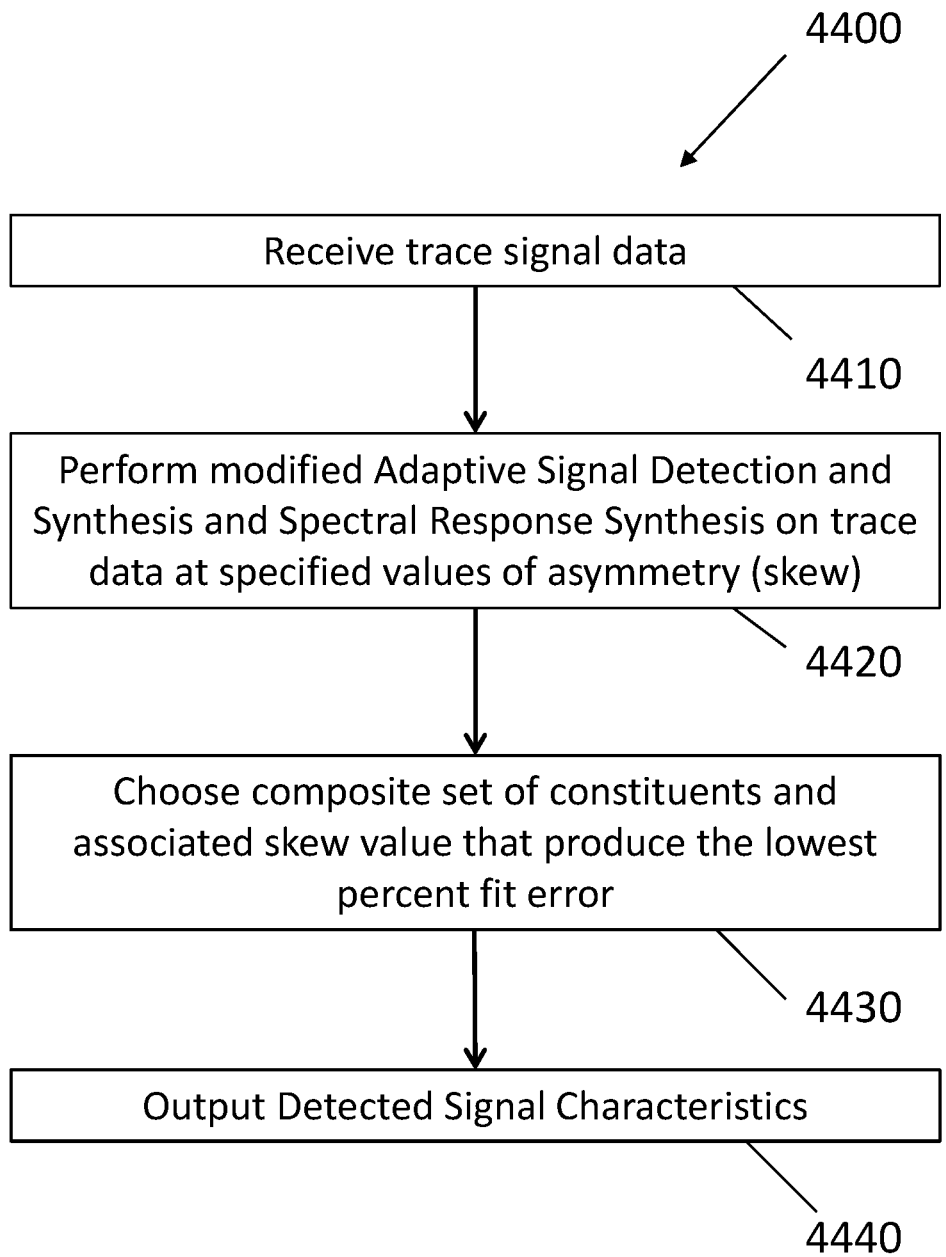

FIG. 44 illustrates a flow diagram of a method for determining constituent signals and the amount of asymmetry (skew) in trace signal data according to an embodiment.

Figure 45:
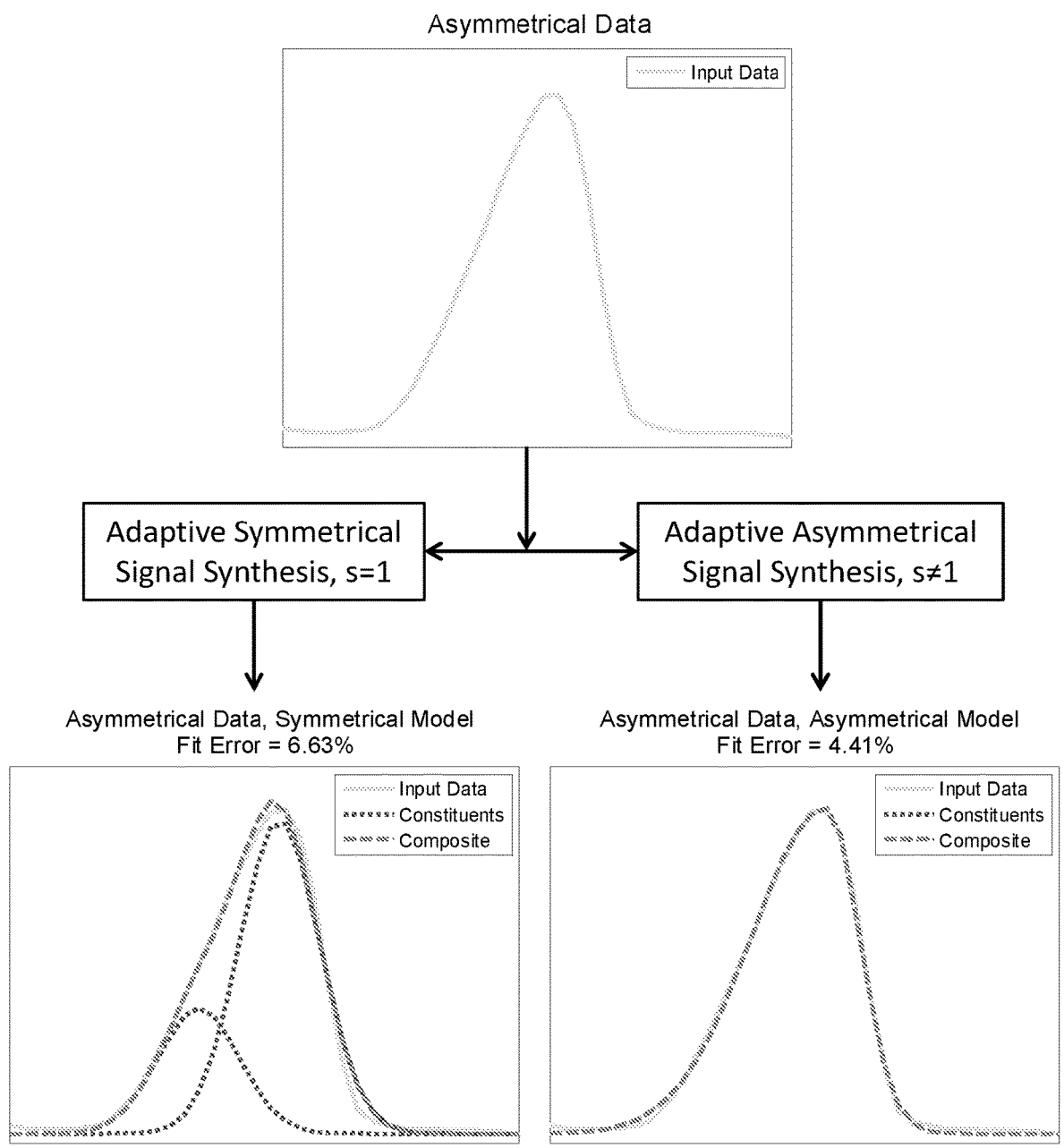

FIG. 45 illustrates an example evaluation of asymmetrical Western Blot trace data using the method of FIG. 44

Figure 46:
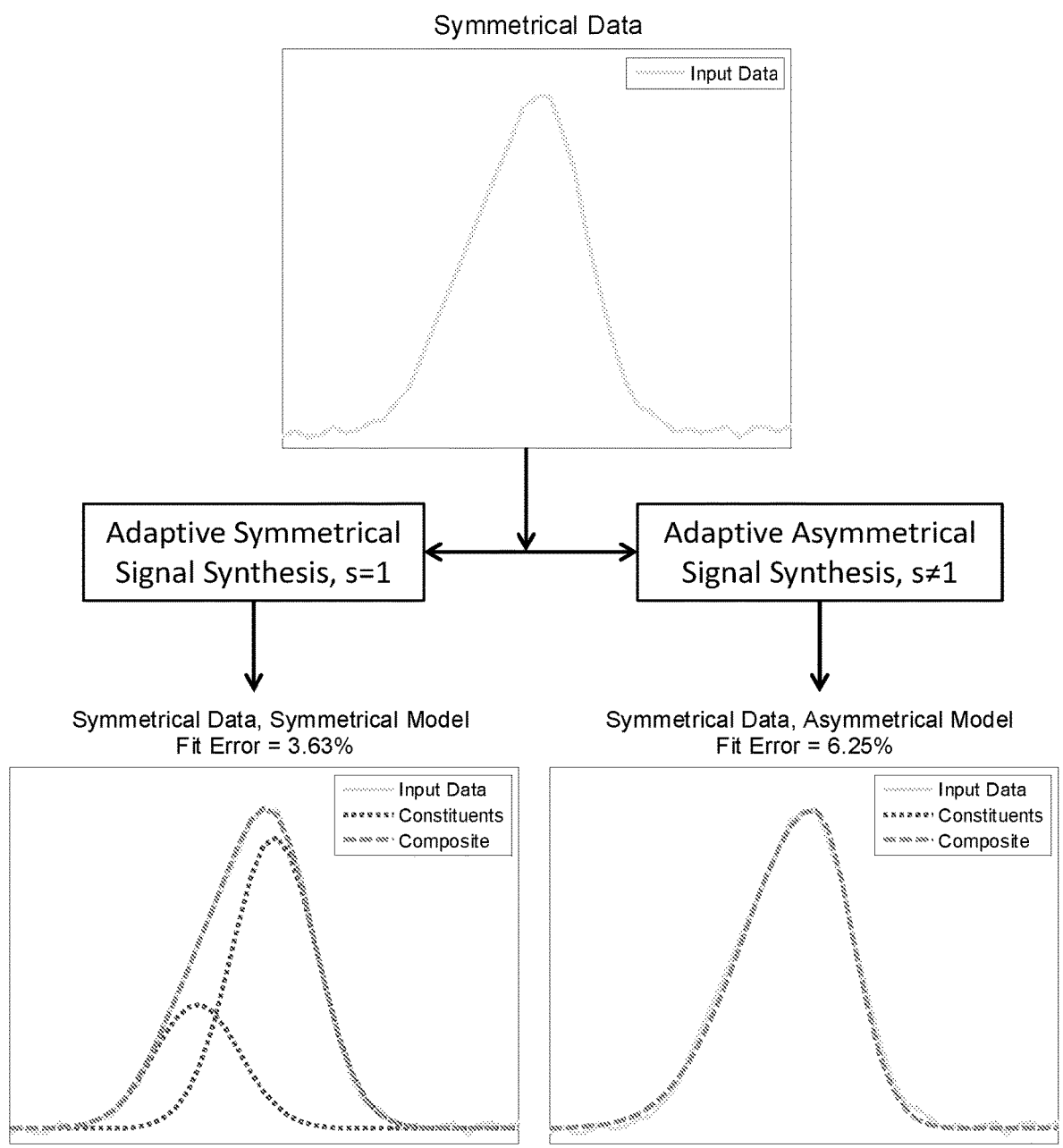

FIG. 46 illustrates an example evaluation of symmetrical trace data using the method of FIG. 44.

Figure 47:
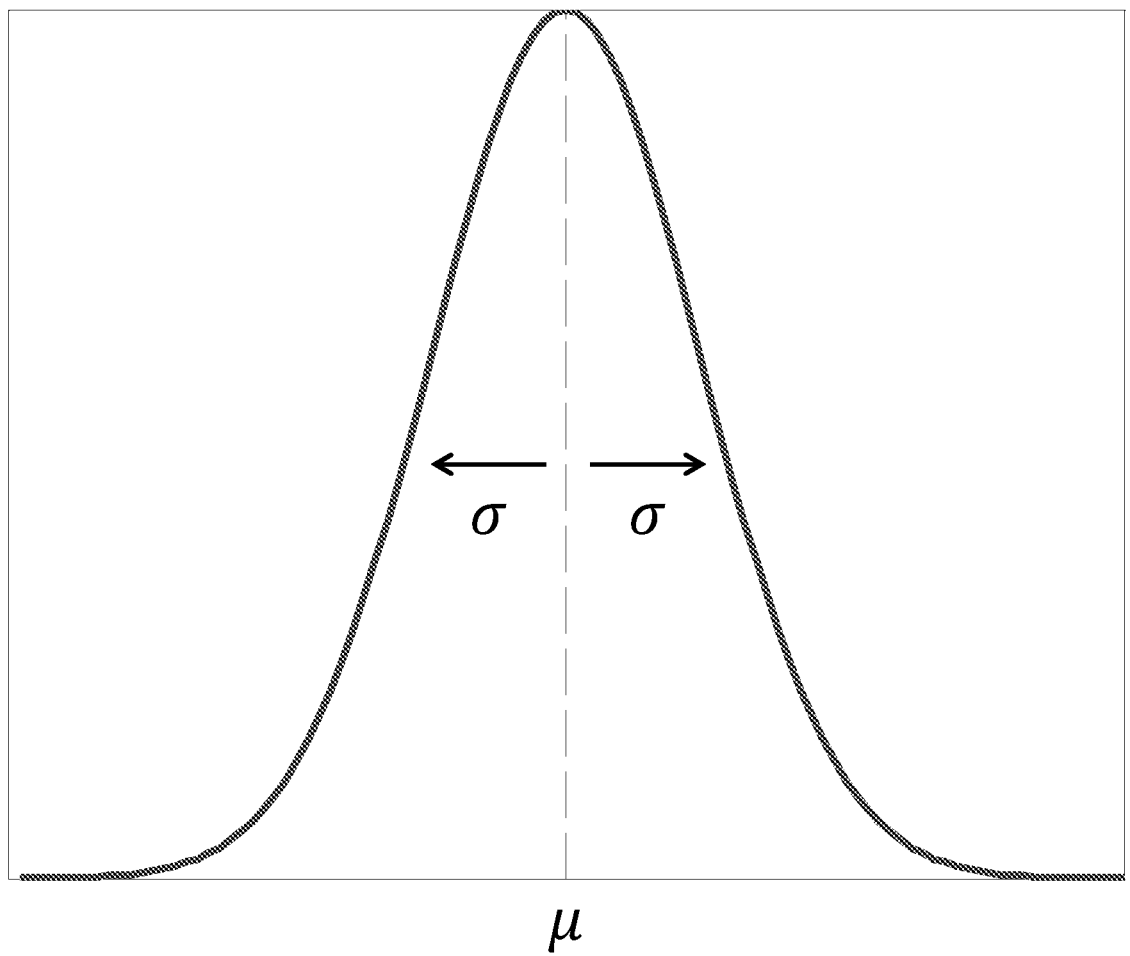

FIG. 47 illustrates that the signal model is symmetrical when s=1.

Figure 48:
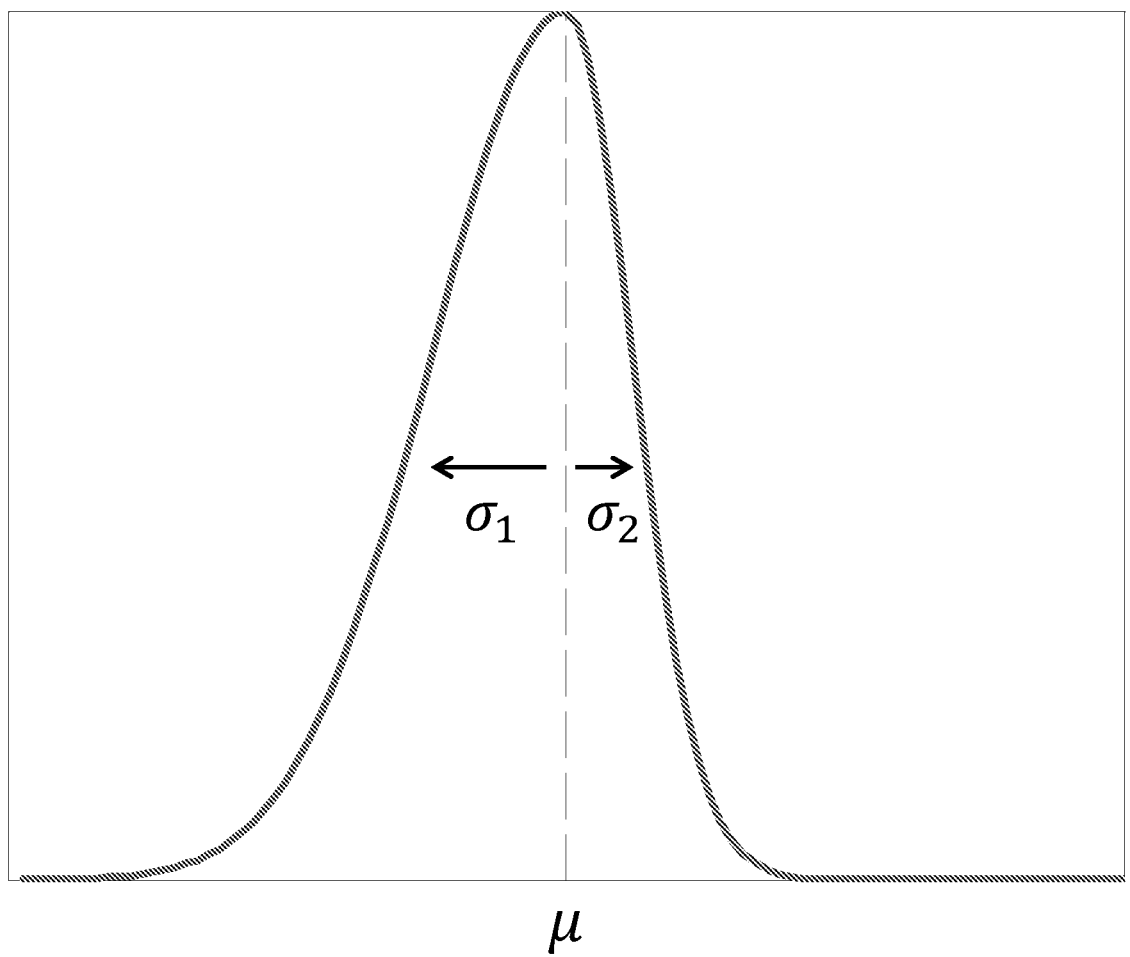

FIG. 48 illustrates that the signal model is skewed when s>1 (when s<1, the signal model is skewed in the opposite direction as shown in FIG. 48).

DETAILED DESCRIPTION

According to various embodiments, techniques for detecting, decoupling and quantifying unresolved constituent signals in trace signal data are automatic and do not require manual user input or configuration. For example, the techniques do not require a priori knowledge of the number of signals or characteristics of the signals, whether overlapping or not, but rather, independently determine underlying data characteristics of the unknown constituent signals on a de novo basis.

The methods are useful for analyzing any data signal having one or multiple constituent signals, and particularly for analyzing electrophoresis data signals, chromatography data signals, spectroscopy data signals, and like signals that often contain an unknown number of signals, often overlapping in frequency, with varying signal characteristics, such as peak location, peak intensity and peak width, varying resolutions, and unknown levels of asymmetry (skew). As one particular example, application of the techniques of the present embodiments to Western blot analysis data enables enhanced measurement of protein expression by providing improved quantitation, throughput, content, reproducibility and signal differentiation.

A general signal model function (e.g., Gaussian, Lorentzian, Voigt, etc.) is assumed for each unknown, constituent signal in the trace signal data. In a first phase, the number of constituent signals and signal characteristics are determined automatically in a parallel fashion by executing multiple simultaneous evaluations iteratively starting with an initial set of trial signals. For example, the initial trial set of possible signals may include all data points, or a subset of all data points, in the trace data. During the first iteration, each trial signal in the set of trial signals (peak locations, intensities, widths) is evaluated simultaneously and the set is systematically reduced to a reduced set of signals. During each iteration thereafter, each signal in the reduced set of signals (peak locations, intensities, widths) is evaluated simultaneously and the set is systematically reduced. Making simultaneous evaluations and systematically reducing the number of trial signals allows for convergence to an optimal, final set of signals in a very fast and efficient manner. In certain aspects, the initial trial signals are assumed to have a specified width, and in a second phase of the methodology of the present disclosure, a width determination process determines an optimal width of the determined constituent signals of the trace signal data, where the width of the signals are assumed to be substantially the same. The systematic signal reduction methodology and signal width determination is advantageously resistant to overfitting of data. In another embodiment, the initial trial signals are not assumed to have a specified width, and may have the same or dissimilar widths; a width determination process determines optimal widths of the determined constituent signals of the trace signal data, where the widths of the signals may be the same or dissimilar. In yet another embodiment, the initial trial signals are not assumed to be symmetric, and may have varying amounts of skew or asymmetry; a skew determination process determines optimal skew values of the determined constituent signals of the trace signal data, where the skew values of the signals may be the same or dissimilar.

Figure 1:
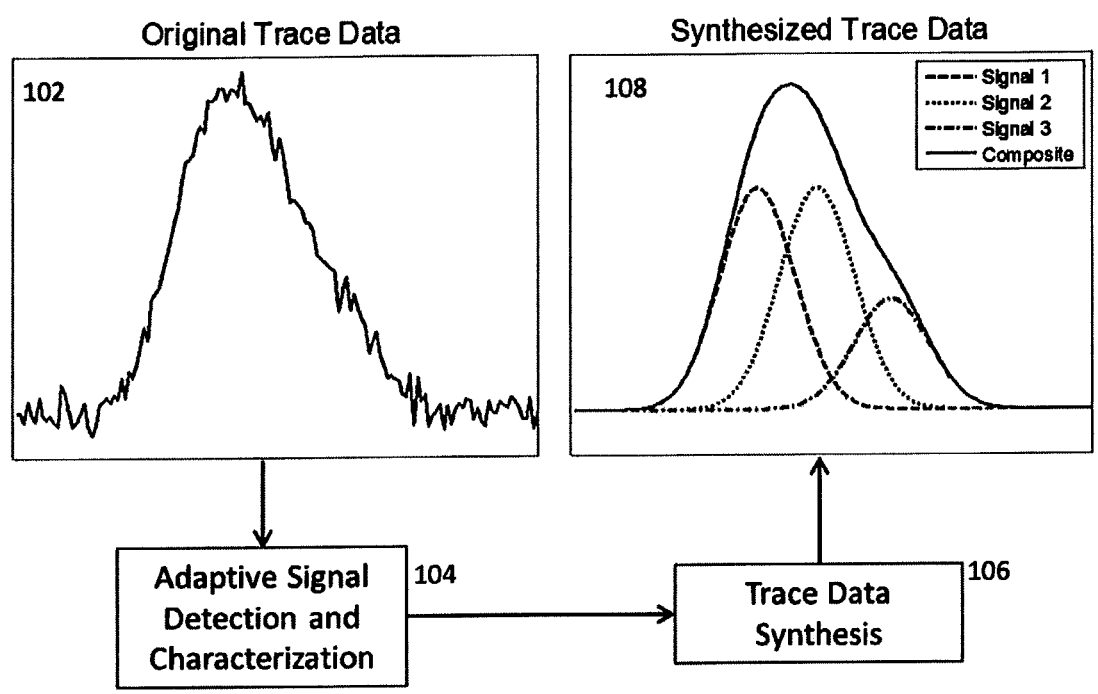
FIG. 1 is a block diagram of an example system for determining constituent signals in trace signal data, according to an embodiment.

FIG. 1 is a block diagram of an example system for determining constituent signals in trace signal data, according to an embodiment. As shown, trace signal data 102 is received. The trace signal data 102 may be input or received from any data generating device and typically includes data representing one or more overlapping signals. Examples of data generating devices include spectroscopic imaging devices (e.g., for analyzing trace gases) or chromatography (liquid or gas) imaging devices or electrophoresis imaging devices or other devices that generate trace signal data including multiple overlapping (in frequency) data signals not listed herein. In general, the embodiments of the present invention are useful for determining and separating properties characterized by, or embodied as, signals. An example might include signals representing automobile or pedestrian traffic flow or traffic flow rates.

The trace signal data 102 is received by a signal detection and characterization engine 104. As described in greater detail herein, the signal detection and characterization engine 104 analyzes the trace signal data 102 to determine and quantify the constituent signals present in the trace signal data 102. Determined information such as the number of constituent signals present and signal characteristics such as peak location, peak amplitude or intensity, asymmetry (skew), and peak width are provided to trace data synthesis engine 106. Trace data synthesis engine 106 processes the signal characteristics to provide an output such as providing data characterizing the constituent signals and/or rendering an output image 108 which represents a visual representation of the trace data signal and its constituent signals. As shown in FIG. 1, for example, trace signal data 102 is determined by the signal detection and characterization engine 104 to have three (3) constituent signals, and trace data synthesis engine 106 renders a display showing the three constituent signals and the composite signal, which represents the signal content of the trace signal data 102. For example, the three constituent signals may represent constituent compounds in electrophoresis trace data, chromatographic trace data, spectrographic trace data, or other produced trace data not listed herein. According to various embodiments, each of the signal detection and characterization engine 104 and/or the trace data synthesis engine 106 can be implemented in hardware, software, and/or a combination of hardware and software. Further, signal detection and characterization engine 104 and trace data synthesis engine 106 may be implemented in the same processing device or in different processing devices.

Figure 2:
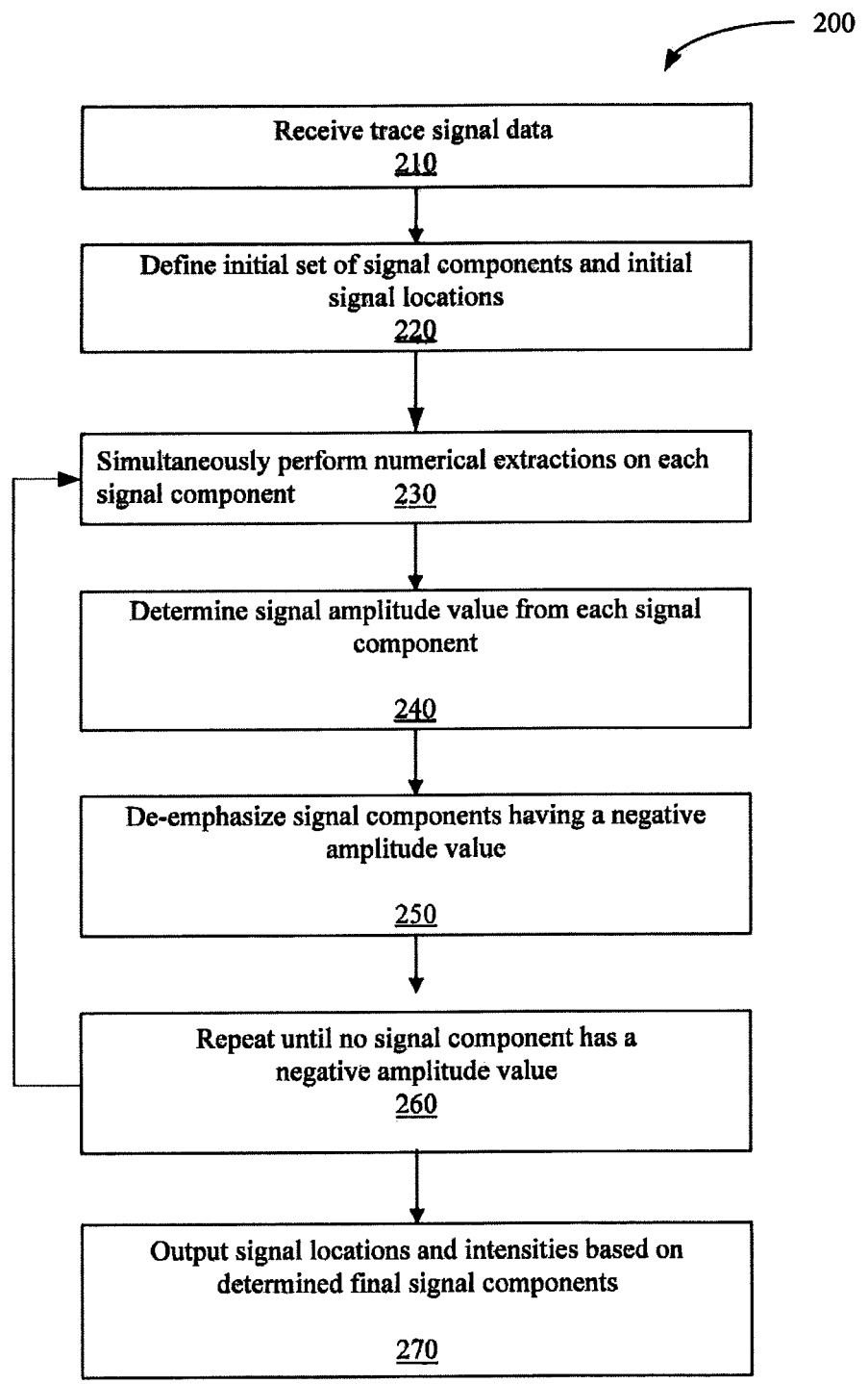
FIG. 2 is a flow diagram for a method (Phase I) of determining the number, location, and intensity (i.e., amplitude) of constituent signals present in trace signal data according to an embodiment.

FIG. 2 is a flow diagram for a method 200 (Phase I) of determining the number, location, and intensity (i.e., amplitude) of constituent signals present in trace signal data according to an embodiment. The unknown, constituent signals of the trace data are each assumed to have the same signal profile (e.g., Gaussian, Lorentzian, etc.) for a specified signal width (or test sigma ($\sigma$)). For example, the optimal signal profile and test width (e.g., test sigma) may be determined automatically based on characteristics of the device or system that generated the trace signal data, or set by a user (e.g., by inputting a signal profile type or selecting from a list of possible signal profile types). Advantageously, the present embodiments do not require a priori knowledge of the number of actual constituent signals in the trace signal data or the characteristics of the constituent signals. For the purposes of discussing the present embodiment, the signals will also be assumed to have no skew; assumed to be symmetric signals. A later described embodiment will focus on determining levels of skew or asymmetry present in the constituent signals.

The method 200 begins at step 210 by signal detection and characterization engine 104 receiving or acquiring the trace signal data 102 to be processed. The trace signal data 102 typically includes a plurality N of data points and represents at least M (unknown, constituent) signal components within the bandwidth defined by the trace data, wherein M is an integer greater than or equal to 1. At step 220, an initial set of signal components (possible constituent signals) is automatically defined based on the trace signal data. For example, an initial set of signal components M for processing is defined as the number N of trace data points in the original data trace where initial signal (peak) locations for each of the signal components of the initial set of signal components correspond to the locations of the number N of data points of the trace signal data. For example, the initial trial signal peak locations are set to be equal to the input data point locations.

Next, the signal amplitude values for all locations are simultaneously calculated to best match the trace signal data. The signals with invalid (e.g., negative) amplitudes are de-emphasized or attenuated to produce an adjusted signal set. For example, in step 230, a numerical method signal extraction calculation is simultaneously performed on each signal component in the initial set of signal components, and at step 240, a signal amplitude value is determined for each signal component of the initial set of signal components based on the extraction calculation. The numerical method extraction calculation may include a conjugate gradient method, a Generalized Minimum Residual method, a Newton's method, a Broyden's method, a Gaussian elimination method or similar method as would be apparent to one skilled in the art. Also, as above, all signal components in the trace data are assumed to have the same curve profile type when performing the numerical method signal extraction calculation.

Examples of curve profile types include a Gaussian profile, a bi-Gaussian profile, an exponentially modified Gaussian profile, a Haarhoff-van der Linde profile, a Lorentzian profile and a Voigt profile.

In step 250, each signal component determined to have a negative signal amplitude value based on the extraction calculation is de-emphasized (e.g., attenuated, or removed) to produce an adjusted set of signal components. The method then recalculates the signal amplitude values with the adjusted signal set. The method continues to systematically adjust (de-emphasize) signals until there are no negative signal amplitudes present, resulting in a final set of signal components (number, locations, and amplitudes) with positive amplitudes that match the signal content of the input trace. For example, in step 260 a final set of signal components is determined by iteratively repeating steps 230, 240 and 250 using, at each iteration, the adjusted set of signal components from the previous iteration as the initial set of signal components until no signal component has a negative amplitude value based on the extraction calculation of step 230. In step 270, information about the final set of signals is output. For example, trace data synthesis engine 106 may output signal peak locations and signal peak intensities of one or more (previously unknown) signal components of the trace signal based on the final set of signal components and/or the trace data synthesis engine 106 may render a visual representation of the overlapping signal components and/or a composite signal representing a combination of the signal components with or without a visual representation of the original trace signal data.

In one embodiment, outputting signal locations and signal intensities of the one or more (previously unknown) signal components of the trace signal data based on the final set of signal components includes identifying one or more amplitude groups in the final set of signal components, where each amplitude group represents a constituent (previously unknown or unresolved) signal component of the trace signal data. In one embodiment, each amplitude group is defined as including final signal components corresponding to one or more consecutive locations each having a non-zero, positive amplitude value. For each amplitude group identified, and hence for each constituent signal of the trace signal data, a signal peak location is determined by calculating a centroid of the corresponding amplitude group. Similarly, for each amplitude group identified, and hence for each constituent signal of the trace signal data, a signal intensity is determined by summing the amplitude values of the final signal components within the corresponding amplitude group.

Figure 3:
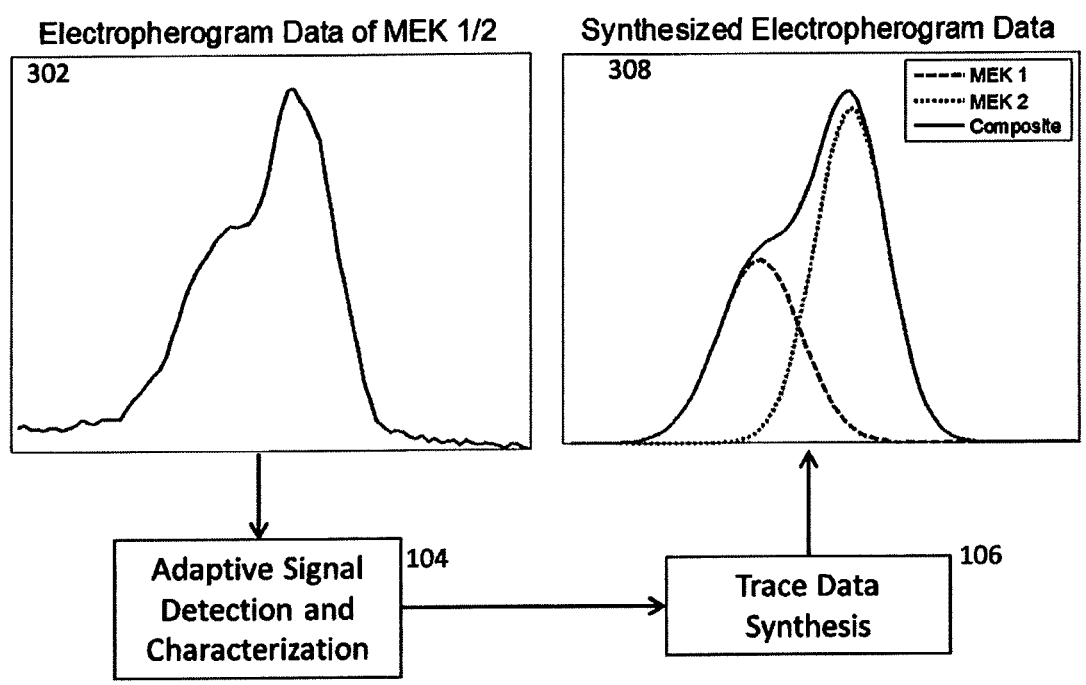
FIG. 3 illustrates an example visual representation of two determined constituent signals MEK 1 and MEK 2 of Electropherogram trace data of MEK 1/2 displayed with a composite signal (combination of MEK1 and MEK2) according to an embodiment.
Figure 4:
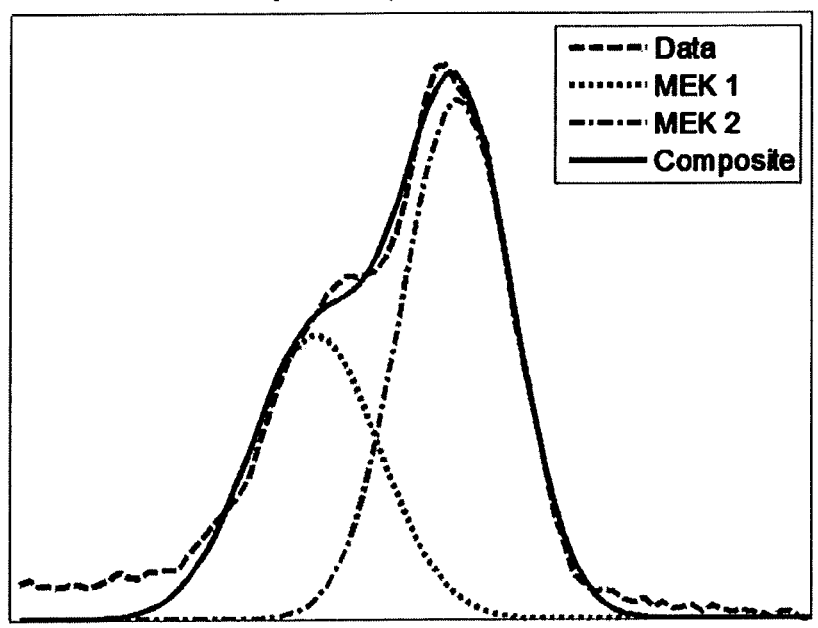
FIG. 4 shows a visual representation of the two constituent signals MEK 1 and MEK 2 displayed with the composite signal and the trace data signal according to an embodiment.
Figure 5:
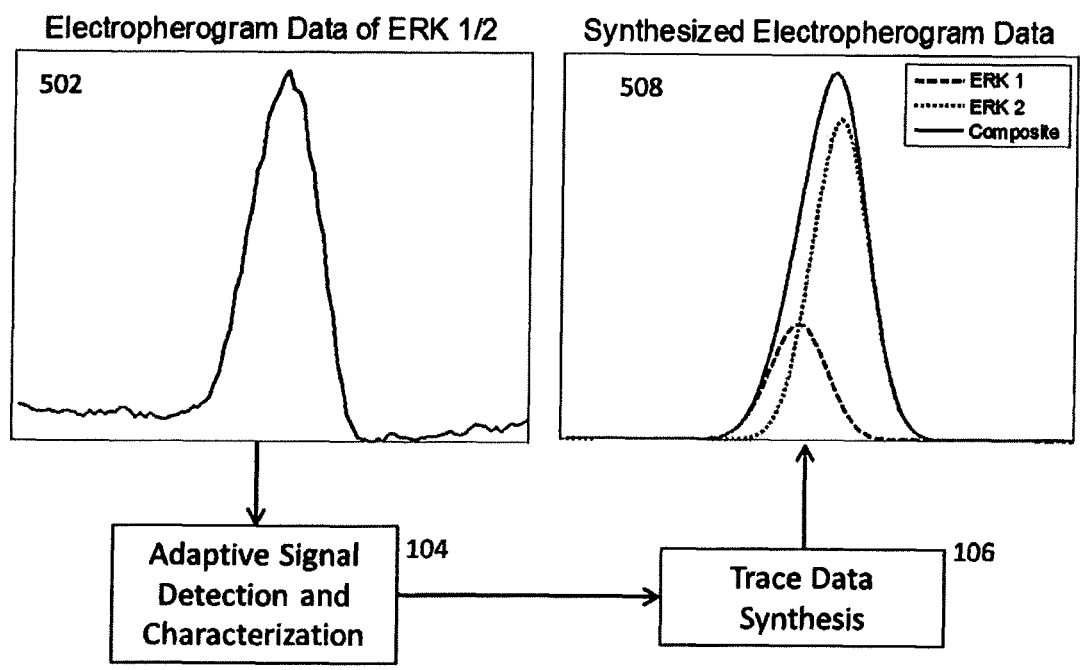
FIG. 5 illustrates an example visual representation of two determined constituent signals ERK 1 and ERK 2 of Electropherogram trace data of ERK 1/2 displayed with a composite signal (combination of ERK1 and ERK2) according to an embodiment.
Figure 6:
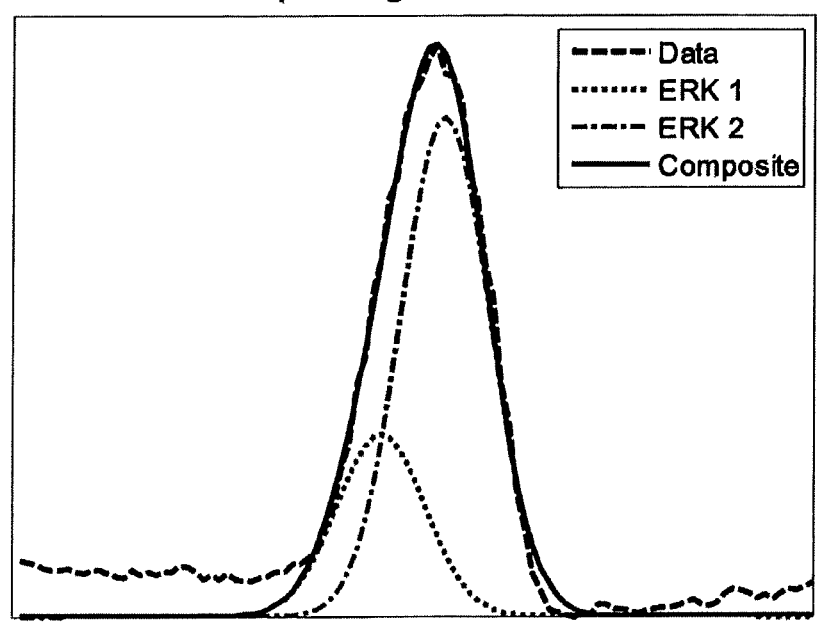
FIG. 6 shows a visual representation of the two constituent signals ERK 1 and ERK 2 displayed with the composite signal and the trace data signal.

FIGS. 3-6 illustrate examples of received trace signal data representing Electropherogram Data of MEK 1/2 (mitogen-activated protein kinases) and Electropherogram Data of ERK 1/2 (extracellular signal-regulated kinases) and visual representations of constituent signals as determined according to the methodology of FIG. 2. FIG. 3 illustrates an example of Electropherogram trace data 302 of MEK 1/2 received and processed by signal detection and characterization engine 104 and a visual representation of two determined constituent signals MEK 1 and MEK 2 displayed with a composite signal 308 (combination of MEK1 and MEK2). FIG. 4 shows a visual representation of the two constituent signals MEK 1 and MEK 2 displayed with the composite signal and the trace signal data 302. As shown, the composite signal 308 substantially matches the trace data signal 302, indicating robustness of the method at accurately detecting and characterizing poorly resolved signals in the presence of noise. FIG. 5 illustrates an example of Electropherogram trace data 502 of ERK 1/2 received and processed by signal detection and characterization engine 104 and a visual representation of two determined constituent signals ERK 1 and ERK 2 displayed with a composite signal 508 (combination of ERK1 and ERK2). FIG. 6 shows a visual representation of the two constituent signals ERK 1 and ERK 2 displayed with the composite signal and the trace data signal 502. As shown, the composite signal 508 substantially matches the trace data signal 502, indicating robustness of the method at accurately detecting and characterizing poorly resolved signals in the presence of noise.

A specific example of a methodology for Phase I, implemented in a matrix formulation, for determining one or more unknown signal components of trace signal data will now be described with reference to FIG. 7. FIG. 7 is a flow diagram of a matrix formulation of a signal detection and synthesis method 700 according to an embodiment. In the embodiment shown in FIG. 7, the constituent signals of the received trace signal data are assumed to have a Gaussian profile and a specified width (test sigma), and the method 700 determines characteristics (e.g., number of signals, location of peaks and amplitudes of peaks) of the constituent signals of the trace signal data.

In step 710 the trace signal data is received. The trace signal data includes a plurality N of data points defined by x and y coordinates (i.e., the bandwidth of the trace signal data is defined by the x-dimension, or range, which may for example be frequency for spectrographic derived data, and the amplitudes are define by the y-dimension). FIG. 8A illustrates a visual representation of trace signal data displayed in a two dimensional x-y graph. As shown in the example of FIG. 8A, the trace signal data has a range of 140 (x=1 to x=140), and for purposes of description will be assumed to include 140 (N) data points. The exemplary Gaussian model may be specified as:

$$\text{Gaussian Model: } G_{(i,j)} = a_i E_{(i,j)} \tag{1}$$

$$E_{(i,j)} = e^{\frac{-[(x_j - \mu_i)/\sigma]^2}{2}} \tag{2}$$

Where $x_j$=trace data point locations
  $y_j$=trace data point intensity values
  $\mu_i$=signal peak (mean) locations
  $\sigma$=signal width (sigma)
  $a_i$=signal peak amplitudes
  i=1 to M (number of constituent signals)
    where M≥1
  j=1 to N (number of data points)

In step 720, the initial number of trial signals are set equal to the number of data points (M=N) or 140 data points in the example of FIG. 8. In step 722, the initial trial signal peak locations ($\mu_i$) are set equal to the input data point locations ($x_j$):($\mu_i = x_j$), and matrix definitions are established or created in one embodiment as follows:

Establish an error squared equal to:

$$Err = \sum_{j=1}^{N} \left( y_j - \sum_{i=1}^{N} a_i E_{(i,j)} \right)^2 \tag{3}$$

and perform a least squares (or other regressive fitting analysis) process which includes differentiation of the error squared (equation (3)) with respect to each of the amplitudes ($a_i$) and setting it equal to zero.

$$\left. \begin{array}{c} \frac{\partial}{\partial a_1}(Err) = \sum_{j=1}^{N} \left( 2 \left( y_j - \sum_{i=1}^{N} a_i E_{(i,j)} \right) E_{(1,j)} \right) = 0 \\ \vdots \qquad \vdots \qquad \vdots \\ \frac{\partial}{\partial a_N}(Err) = \sum_{j=1}^{N} \left( 2 \left( y_j - \sum_{i=1}^{N} a_i E_{(i,j)} \right) E_{(N,j)} \right) = 0 \end{array} \right\} \tag{4}$$

Rewrite equation (4) as:

$$\left. \begin{array}{c} a_1 \sum_{j=1}^{N} (E_{(1,j)} E_{(1,j)}) + \ldots + a_N \sum_{j=1}^{N} (E_{(N,j)} E_{(1,j)}) = \sum_{j=1}^{N} (y_j E_{(1,j)}) \\ \vdots \qquad \vdots \qquad \vdots \\ a_1 \sum_{j=1}^{N} (E_{(1,j)} E_{(N,j)}) + \ldots + a_N \sum_{j=1}^{N} (E_{(N,j)} E_{(N,j)}) = \sum_{j=1}^{N} (y_j E_{(N,j)}) \end{array} \right\} \tag{5}$$

In step 724 matrices a, C and b are initialized as follows:

$$a = \begin{bmatrix} a_1 \\ \vdots \\ a_N \end{bmatrix} \quad (6)$$

$$C = \begin{bmatrix} \sum_{j=1}^{N}(E_{(1,j)}E_{(1,j)}) & \cdots & \sum_{j=1}^{N}(E_{(N,j)}E_{(1,j)}) \\ \vdots & \ddots & \vdots \\ \sum_{j=1}^{N}(E_{(1,j)}E_{(N,j)}) & \cdots & \sum_{j=1}^{N}(E_{(N,j)}E_{(N,j)}) \end{bmatrix} \quad (7)$$

$$b = \begin{bmatrix} \sum_{j=1}^{N}(y_j E_{(1,j)}) \\ \vdots \\ \sum_{j=1}^{N}(y_j E_{(N,j)}) \end{bmatrix} \quad (8)$$

so that equation (5) can be written as:

$$Ca = b \quad (9)$$

In step 726 a weighting matrix w is defined and initialized as:

$$w = \begin{bmatrix} w_1 \\ \vdots \\ w_M \end{bmatrix} \quad (10)$$

Weighting matrix w advantageously allows for selectively and iteratively weighting the significance of each signal. Each weighting w has a value between 0 and 1, inclusive, where a weighting of 0 would represent complete removal, and a weighting of 1 would represent no reduction or de-emphasis. In certain aspects, the weightings can vary with each iteration and weightings can vary consistently across all indices, (all weightings change by the same amount) or differently across all indices, (e.g., one or more particular weightings may change by different values at each iteration). In the first iteration, the weightings should all be set to 1 (but they need not be).

In step 730 a Signal Extraction Matrix (H) is calculated by defining:

$$H = Iw \quad (11)$$

I=M by M identity matrix
and updating equation (9) with Signal Extraction Matrix as follows:

$$[HCH]a = Hb \quad (12)$$

In step 740, the amplitudes ($a_1$) are solved for in equation (12) utilizing a numerical method such as conjugate gradient process or other useful method. Other useful numerical methods include a Generalized Minimum Residual method, a Newton's method, a Broyden's method, a Gaussian elimination method and the like. At decision step 744, if any of the determined amplitudes are negative, the amplitude indices corresponding to the negative amplitudes are established or identified at step 746. In step 750, the weight values ($w_i$) with the corresponding indices (negative amplitudes) are multiplied by an attenuation factor (0≤attenFactor<1). The Signal Extraction Matrix (H) is then recalculated with the updated weighting matrix (w) in step 730. The amplitudes are then recalculated in step 740 utilizing equation (12) with the updated matrices. If any of the recalculated amplitudes are negative, the process (update (w) and (H) matrices and recalculate amplitudes) is repeated until each and every one of the calculated amplitudes are greater than or equal to zero. In this manner, the initial number of potential (trial) signals (N) has been systematically reduced to a final number of potential signals, e.g., the number of amplitudes ($a_i$) that are non-zero and positive. If, at decision step 744, all remaining amplitude values are non-negative (greater than or equal to zero), the method proceeds to step 770, where relevant information regarding the final signals are processed or output. For example, the number of constituent signals, peak locations and/or amplitudes or intensities of the constituent signals may be output at step 770.

In one embodiment, for example, the final, constituent signals are determined by detecting amplitude groups, where a group is defined as one or more consecutive (no gaps) non-zero positive amplitudes ($a_i$). In one embodiment, the signal locations of the constituent signals are the calculated centroids of each amplitude group, and the intensity of each constituent signal is equal to the summation of the amplitudes within each respective amplitude group.

FIGS. 8A-8E and FIGS. 9A-9E illustrate examples of processing a trace signal according to method 700 according to embodiments. In FIGS. 8A-8ES. 9A-9E, the trace signal data is noisy/includes noise.

FIG. 8A shows the original trace signal data comprising 140 data points. FIG. 8B shows the reduced set of trial signals after two processing iterations of process 700 (specifically steps 730 to 750). FIG. 8C shows the reduced set of trial signals after eight processing iterations of process 700. As can be seen in FIG. 8C, the signals are beginning to converge to three groups. The negative amplitude values shown in FIG. 8C are de-emphasized in step 750 upon the next iteration. FIG. 8D shows the reduced set of trial signals after N (not N as in the number of trace data points, but rather a generic value N which in this case may be 11 or 12) processing iterations of process 700. As can be seen in FIG. 8D, three amplitude groups have emerged, where these three amplitude groups can be processed to determine characteristics of three constituent signals. FIG. 8E shows a visual representation of the three constituent signals and their determined characteristics (i.e., peak location, peak intensity and width (in this case the specified test sigma)) and also a visualization of the sum of the three constituent signals, which matches the original trace signal data shown in FIG. 8A.

FIG. 9A shows the original trace signal data comprising 140 data points. The trace signal data in FIG. 9A is similar to that of FIG. 8A, but includes noise. FIG. 9B shows the reduced set of trial signals after two processing iterations of process 700 (specifically steps 730 to 750). FIG. 9C shows the reduced set of trial signals after eight processing iterations of process 700. As can be seen in FIG. 9C, the signals are beginning to converge to three groups. The negative amplitude values shown in FIG. 9C are de-emphasized in step 750 upon the next iteration. FIG. 9D shows the reduced set of trial signals after N (not N as in the number of trace data points, but rather a generic value N which in this case may be 11 or 12) processing iterations of process 700. As can be seen in FIG. 9D, three amplitude groups have emerged, where these three amplitude groups can be processed to determine characteristics of three constituent signals. FIG. 9E shows a visual representation of the three constituent signals and their determined characteristics (i.e., peak location, peak intensity and width (in this case the specified test sigma)) and also a visualization of the sum of the three constituent signals, which substantially matches the original trace signal data shown in FIG. 9A, but without the noise which has effectively been filtered out, e.g., by implementation of process 700.

In some instances, it is desirable to determine an optimal width of the constituent signals determined in Phase I. Phase II of the method, in conjunction with Phase I, determines the optimal signal width (sigma) and the associated number of signals, locations, and amplitudes of each of the signals (which are assumed to be Gaussian) contained within the input trace data. In one embodiment, a set of trial (test) signal widths are processed individually in Phase I (method 700) and are evaluated together as a set to determine the optimal signal sigma (and the associated number of signals, locations, and amplitudes). For example, in one embodiment, a plurality of test signal width values are defined and Phase I process 700 is repeated for each of the plurality of test signal width values and the results of each Phase I output are evaluated together to determine an optimal signal width for each of the one or more signal components of the trace signal. The test signal width values may be defined automatically based on characteristics of the device or system that generated the trace signal data, or set by a user (e.g., by inputting specific test sigma values, or a range of values, or selecting from a list of possible values or range of values).

A specific example of a methodology for Phase II, implemented in a matrix formulation, for determining one or more unknown signal components of trace signal data will now be described with reference to FIG. 10. FIG. 10 is a flow diagram of a matrix formulation of a signal width (sigma) determination method 1000 according to an embodiment. In method 1000, the exemplary Gaussian model shown in FIG. 7 is updated to include multiple signal widths as follows:

$$\text{Gaussian Model: } G_{(i,j,k)} = A_{(i,k)}E_{(i,j,k)} \quad (13)$$

$$E_{(i,j,k)} = e^{\frac{-[(x_j-\mu_i)/\sigma_k]^2}{2}} \quad (14)$$

where $x_j$=trace data point locations
$y_j$=trace data point intensity values
$\mu_i$=signal peak (mean) locations
$A_{(i,k)}$=signal peak amplitude matrix
$\sigma_k$=signal test widths (sigmas)
i=1 to M (number of signals)
j=1 to N (number of data points)
k=1 to P (number of test signal widths (sigmas))

In step 1010, the trace signal data is received and a plurality (e.g., two or more) test signal widths are received. The test signal widths (test sigma ($\sigma_k$)) may be received from a user input, or may be automatically generated by the system. In step 1020, the Phase I method 700 is performed for each test sigma ($\sigma_k$) resulting in a set of amplitudes ($A_{(i,k)}$) for each data point location ($x_j$) and sigma ($\sigma_k$). In Phase I method 700 the number of initial peaks (M) is equal to the number of data points (N) and the initial signal peak locations ($\mu_i$) are set equal to the trace data point locations ($x_j$).

In step 1030, the amplitude outputs ($A_{(i,k)}$) from the multi-Phase I analysis, step 1020, are synthesized into a set of fit traces. In one embodiment, the fit traces are synthesized as follows:

$$yFit_{(j,k)} = \sum_{i=1}^{N} A_{(i,k)}E_{(i,j,k)} \quad (15)$$

In step 1040, a region (r) along the trace data location axis ($x_j$) is selected where there is activity (e.g., amplitudes>0) and where the signal widths are deemed to be stable (e.g., not varying by more than a defined threshold percentage). For this example the region will be defined as equivalent to the trace data locations ($r_j$=$x_j$).

In step 1050, trace fit quality metrics are determined. For example, in one embodiment, a trace percent fit error is calculated for each test sigma ($\sigma_k$) as follows:

$$PE_k = \frac{100\sum_{j=1}^{N}|y_j - yFit_{(j,k)}|}{\sum_{j=1}^{N} y_j} \quad (16)$$

where a perfect match occurs when ($PE_k$=0), and a trace fit peak count ratio is calculated for each test sigma ($\sigma_k$) as follows:

$$PC_k = \frac{\text{number of amplitudes } (A_{(i,k)}) \text{ for each } \sigma_k}{N} \quad (17)$$

In step 1060, an optimal sigma fit factor is calculated, for example, by normalizing equations (16) and (17), and summing them accordingly:

$$SF_k = \frac{PE_k - \min(PE_k)}{\max(PE_k) - \min(PE_k)} + \frac{PC_k - \min(PC_k)}{\max(PC_k) - \min(PC_k)} \quad (18)$$

Locating the minimum of $SF_k$ provides an indication of the optimal signal width (sigma) for that trace data region. If other data regions have not been processed, the method proceeds to step 1040 for the additional data region(s).

In step 1070, detected signal characteristics (e.g., peak locations and intensities from Phase I and peak widths from Phase II) are output. Step 1070 may be performed after each data region (r) has been processed or after all data regions have been processed. The number of signals (groups of consecutive amplitudes with intensities greater than zero), locations (centroid location of each amplitude group), and intensities (amplitude group sum) has been established. These determined signal characteristics can then be synthesized to describe the signal content of the input trace signal data.

FIGS. 11A-11C and FIGS. 15A-15C provide examples illustrating the processing (fit error) results for three test signal widths (sigmas), without and with noise, respectively, in the Phase II method 1000 for which the true sigma width is 10.

FIGS. 11A-11C, 12, 13 and 14 illustrate example Phase II results for trace signal data without noise. FIG. 11A-11C illustrate (fit error or $PE_k$) results for three test signal widths (sigmas) for trace signal data without noise, where the true signal width (sigma) is 10. FIG. 11A shows results for a test sigma of 6 with a fit error of 0, FIG. 11B shows results for a test sigma of 10, with a fit error of 0, and FIG. 11C shows results for a test sigma of 14, with a fit error of 5.04. FIG. 12 illustrates a graph of fit error (or $PE_k$) v. test sigma from trace data containing Gaussian signals for a range of test sigmas (5 to 15). As can be seen, the slope of the curve deviates where the test signal width (sigma) equals the true signal width (sigma), in this example 10. FIG. 13 illustrates a graph of peak count ratio (or $PC_k$) v. test sigma from trace data containing Gaussian signals for a range of test sigmas (5 to 15). As can be seen, the slope of the curve deviates where the test signal width (sigma) equals the true signal width (sigma), in this example 10. FIG. 14 illustrates a graph of calculated sigma fit factor (or $SF_k$) v. test sigma from trace data containing Gaussian signals for a range of test sigmas (5 to 15). As can be seen, the vertex (dip) in the curve occurs where the test signal width (sigma) equals the true signal width (sigma), in this example 10.

FIGS. 15A-15C, 16, 17 and 18 illustrate example Phase II results for trace signal data in the presence of noise. FIGS. 15A-15C illustrates (fit error or $PE_k$) results for three test signal widths (sigmas) for trace signal data in the presence of noise, where the true signal width (sigma) is 10. FIG. 15A shows results for a test sigma of 6 with a fit error of 6.23, FIG. 15B shows results for a test sigma of 10 with a fit error of 6.31, and FIG. 15C shows results for a test sigma of 14, with a fit error of 8.44. FIG. 16 illustrates a graph of fit error (or $PE_k$) v. test sigma from trace data containing Gaussian signals for a range of test sigmas (5 to 15). As can be seen, the slope of the curve deviates where the test signal width (sigma) equals the true signal width (sigma), in this example 10. FIG. 17 illustrates a graph of peak count ratio (or $PC_k$) v. test sigma from trace data containing Gaussian signals for a range of test sigmas (5 to 15). As can be seen, the slope of the curve deviates where the test signal width (sigma) equals the true signal width (sigma), in this example 10. FIG. 18 illustrates a graph of calculated sigma fit factor (or $SF_k$) v. test sigma from trace data containing Gaussian signals for a range of test sigmas (5 to 15). As can be seen, the vertex (dip) in the curve occurs where the test signal width (sigma) equals the true signal width (sigma), in this example 10.

FIG. 19 is a block diagram of example functional components for a computing system or device 1902 configured to perform one or more of the analysis techniques described herein above or below, according to an embodiment. For example, the computing device 1902 may be configured to analyze an input data stream (trace signal data) and to determine one or more (unknown) constituent signals in the input data stream. One particular example of computing device 1902 is illustrated. Many other embodiments of the computing device 1902 may be used. In the illustrated embodiment of FIG. 19, the computing device 1902 includes one or more processor(s) 1911, memory 1912, a network interface 1913, one or more storage devices 1914, a power source 1915, output device(s) 1960, and input device(s) 1980. The computing device 1902 also includes an operating system 1918 and a communications client 1940 that are executable by the computing device 1902. Each of components 1911, 1912, 1913, 1914, 1915, 1960, 1980, 1918, and 1940 is interconnected physically, communicatively, and/or operatively for inter-component communications in any operative manner.

As illustrated, processor(s) 1911 are configured to implement functionality and/or process instructions for execution within computing device 1902. For example, processor(s) 1911 execute instructions stored in memory 1912 or instructions stored on storage devices 1914. The processor may be implemented as an ASIC including an integrated instruction set. Memory 1912, which may be a non-transient computer-readable storage medium, is configured to store information within computing device 1902 during operation. In some embodiments, memory 1912 includes a temporary memory, area for information not to be maintained when the computing device 1902 is turned OFF. Examples of such temporary memory include volatile memories such as random access memories (RAM), dynamic random access memories (DRAM), and static random access memories (SRAM). Memory 1912 maintains program instructions for execution by the processor(s) 1911. Example programs can include the signal detection and characterization engine 104 and/or the trace data synthesis engine 106 in FIG. 1.

Storage devices 1914 also include one or more non-transient computer-readable storage media. Storage devices 1914 are generally configured to store larger amounts of information than memory 1912. Storage devices 1914 may further be configured for long-term storage of information. In some examples, storage devices 1914 include non-volatile storage elements. Non-limiting examples of non-volatile storage elements include magnetic hard disks, optical discs, floppy discs, flash memories, or forms of electrically programmable memories (EPROM) or electrically erasable and programmable (EEPROM) memories.

The computing device 1902 uses network interface 1913 to communicate with external devices via one or more networks. Network interface 1913 may be a network interface card, such as an Ethernet card, an optical transceiver, a radio frequency transceiver, or any other type of device that can send and receive information. Other non-limiting examples of network interfaces include wireless network interface, Bluetooth®, 9G and WiFi® radios in mobile computing devices, and USB (Universal Serial Bus). In some embodiments, the computing device 1902 uses network interface 1913 to wirelessly communicate with an external device or other networked computing device.

The computing device 1902 includes one or more separate or integrated input devices 1980. Some input devices 1980 are configured to sense the environment and capture images or other signals. Some input devices 1980 are configured to receive input from a user through tactile, audio, video, or other sensing feedback. Non-limiting examples of input devices 1980 include a presence-sensitive screen, a mouse, a keyboard, a voice responsive system, camera 1903, a video recorder 1904, a microphone 1906, a GPS module 1908, or any other type of device for detecting a command from a user or for sensing the environment. In some examples, a presence-sensitive screen includes a touch-sensitive screen.

One or more output devices 1960 are also included in computing device 1902. Output devices 1960 are configured to provide output to another system or device or to a user using tactile, audio, and/or video stimuli. Output devices 1960 may include a display screen (e.g., a separate screen or part of the presence-sensitive screen), a sound card, a video graphics adapter card, or any other type of device for converting a signal into an appropriate form understandable to humans or machines. Additional examples of output device 1960 include a speaker, a cathode ray tube (CRT) monitor, a liquid crystal display (LCD), or any other type of device that can generate intelligible output to a user. In some embodiments, a device may act as both an input device and an output device.

The computing device 1902 includes one or more power sources 1915 to provide power to the computing device 1902. Non-limiting examples of power source 1915 include single-use power sources, rechargeable power sources, and/or power sources developed from nickel-cadmium, lithium-ion, or other suitable material.

The computing device 1902 includes an operating system 1918. The operating system 1918 controls operations of the components of the computing device 1902. For example, the operating system 1918 facilitates the interaction of communications client 1940 with processors 1911, memory 1912, network interface 1913, storage device(s) 1914, input device 1980, output device 1960, and power source 1915.

As also illustrated in FIG. 19, the computing device 1902 includes communications client 1940. Communications client 1940 includes communications module 1945. Each of communications client 1940 and communications module 1945 includes program instructions and/or data that are executable by the computing device 1902. For example, in one embodiment, communications module 1945 includes instructions causing the communications client 1940 executing on the computing device 1902 to perform one or more of the operations and actions described in the present disclosure. In some embodiments, communications client 1940 and/or communications module 1945 form a part of operating system 1918 executing on the computing device 1902.

According to various embodiments, one or more of the components shown in FIG. 19 may be omitted from the computing device 1902.

According to another embodiment, a Spectral Response Synthesis (SRS) methodology is provided that can not only detect and characterize signal components within a region that have the same or similar signal widths but also signal components having dissimilar signal widths. This is accomplished, in certain embodiments, by subjecting the input trace data to the Phase I method (e.g., method 700), for each of a plurality of defined test signal width values, resulting in spectral response data for each of the test signal width values used in Phase I. The spectral response data for each of the test signal width values used in Phase I includes a signal location for each of one or more detected signal components. The spectral response data for each of the test signal width values are then synthesized to form a composite spectral response, which represents the varying signal widths for a given input trace region. For example, for data characterized by Gaussian signals the spectral response data may be referred to as Gaussian spectral response data.

The ability to detect signals with varying signal widths is significant in that data generated from spectroscopy, chromatography and electrophoresis, as examples, often contains overlapping signals with dissimilar signal widths. Additionally, the input data trace may contain signals with widths that vary by up to a factor of three (3) to four (4) times or more. The present embodiments are able to automatically determine these varying signal characteristics with no prior knowledge of the signal characteristics, other than the general signal shape (e.g., Gaussian or other shape).

A block diagram of an exemplary system for determining constituent signals having the same or dissimilar widths in trace signal data is illustrated in FIG. 20. As shown, trace signal data 2002 is received. The trace signal data 2002 may be input or received from any data generating device or data storage device and typically includes data representing one or more signals, which may include overlapping signals. Examples of data generating devices include spectroscopic imaging devices (e.g., for analyzing trace gases) or chromatography (liquid or gas) imaging devices or electrophoresis imaging devices or other devices that generate trace signal data including multiple overlapping (in frequency) data signals. In general, the embodiments of the present invention are useful for determining and separating properties characterized by, or embodied as, signals. An example might include signals representing automobile or pedestrian traffic flow or traffic flow rates.

The trace signal data 2002 is received by a signal detection and characterization engine 2004. As described in greater detail herein, and also similar to the signal detection and characterization engine 104 described above, signal detection and characterization engine 2004 analyzes the trace signal data 2002 to determine and quantify the constituent signals present in the trace signal data 2002. Determined information, such as the number of constituent signals present and signal characteristics such as peak location, peak amplitude or intensity, and peak width, for each constituent signal is provided to trace data synthesis engine 2006. Trace data synthesis engine 2006 processes the signal characteristics to provide an output such as providing data characterizing the constituent signals and/or rendering an output image 2008 which represents a visual representation of the trace data signal and its determined constituent signals. As shown in FIG. 20, for example, trace signal data 2002 is determined by the signal detection and characterization engine 2004 to have seven (7) constituent signals, and trace data synthesis engine 2006 renders a display showing the seven (7) constituent signals and the composite signal, which represents the signal content of the trace signal data 2002. For example, the seven (7) constituent signals may represent constituent compounds in electrophoresis trace data, chromatographic trace data, or spectrographic trace data. According to various embodiments, each of the signal detection and characterization engine 2004 and/or the trace data synthesis engine 2006 can be implemented in hardware, software, and/or a combination of hardware and software. Further, signal detection and characterization engine 2004 and trace data synthesis engine 2006 may be implemented in the same processing device or in different processing devices.

FIG. 21 is a flow diagram for a method 2000 of determining the number, location, intensity (i.e., amplitude), and width of each of one or more constituent signal present in trace signal data 2002 according to an embodiment. The unknown, constituent signals of the trace data are assumed to have the same signal profile (e.g., Gaussian, Lorentzian, etc). For example, the optimal signal profile may be determined automatically based on characteristics of the device or system that generated the trace signal data, or set by a user (e.g., by inputting a signal profile type or selecting from a list of possible signal profile types as defined herein). Advantageously, the present embodiments do not require a priori knowledge of the number of actual constituent signals in the trace signal data or the characteristics of the constituent signals.

The method 2000 begins at step 2010 by signal detection and characterization engine 2004 receiving or acquiring the trace signal data 2002 to be processed. The trace signal data 2002 typically includes a plurality N of data points and represents at least M (unknown, constituent) signal components within the bandwidth defined by the trace data, wherein M is an integer greater than or equal to 1.

The (unknown) signal width of a constituent signal can be defined as equal to the full width at half the maximum (FWHM) amplitude of the constituent signal. For a Gaussian signal, for example, the signal FWHM can be expressed as a function of the Gaussian signal standard deviation ($\sigma$) as shown in Equation 19 as follows:

$$FWHM = 2 \times \sqrt{-2\sigma^2 \ln(0.5)} \qquad (19)$$

The Gaussian signal standard deviation (σ) can be expressed as a function of the FWHM shown in Equation 20 as follows:

$$\sigma = \frac{1}{2} \times \sqrt{\frac{(FWHM)^2}{-2\ln(0.5)}} \qquad (20)$$

Figure 23:
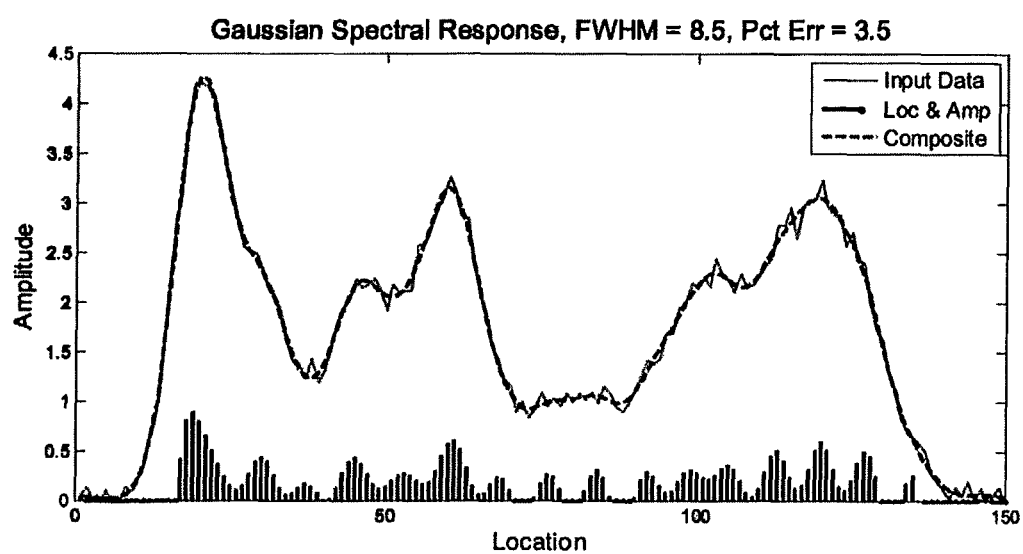
Figure 24:
Figure 25:
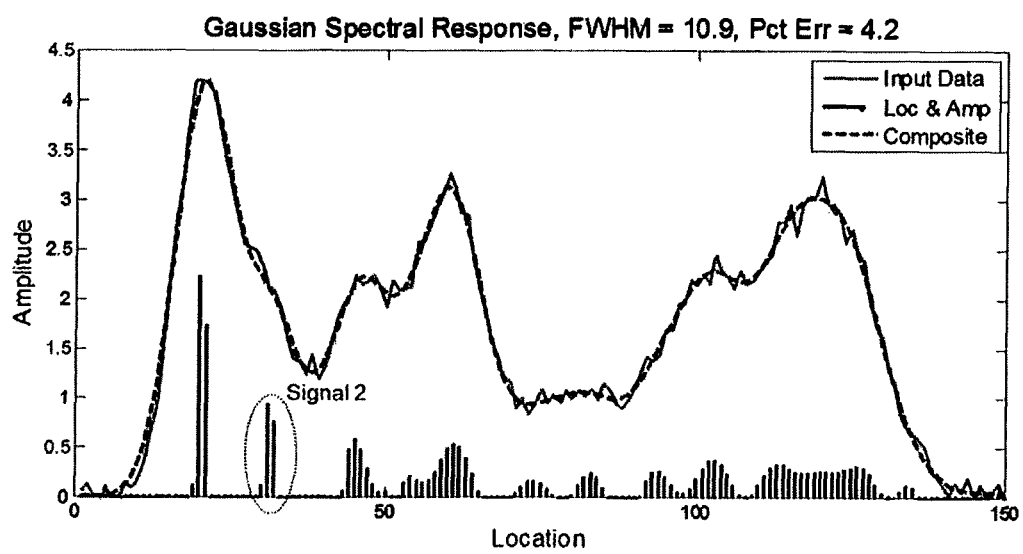
Figure 26:
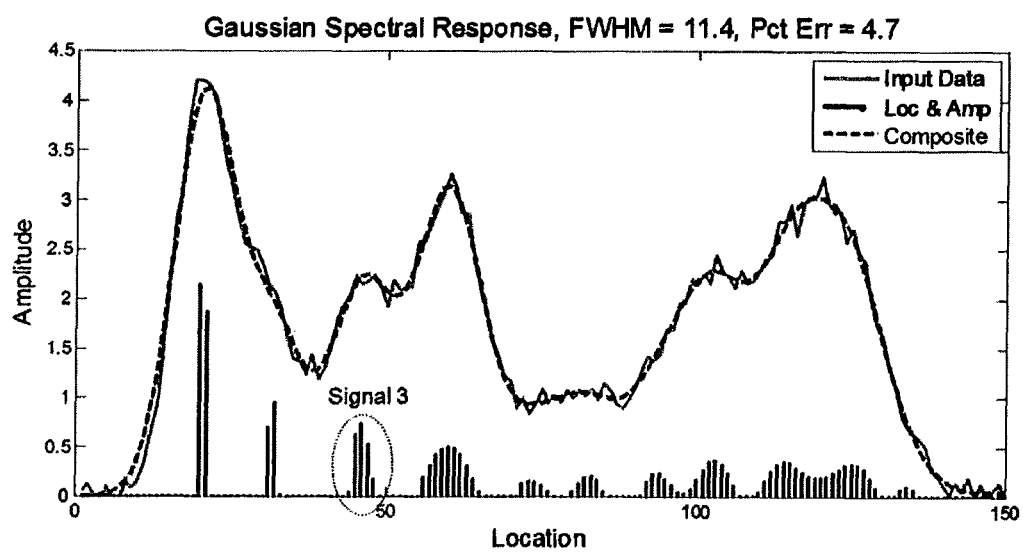
Figure 27:
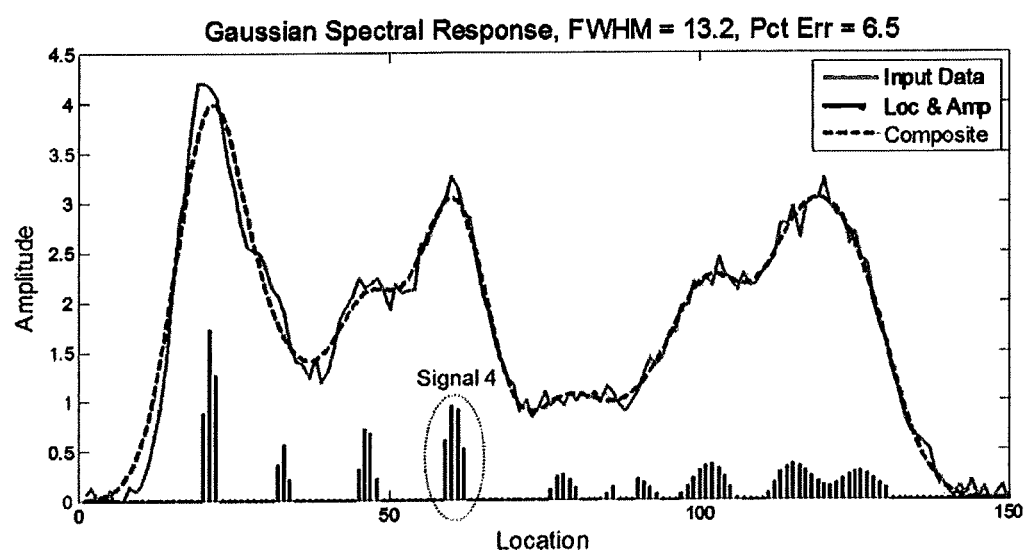
Figure 28:
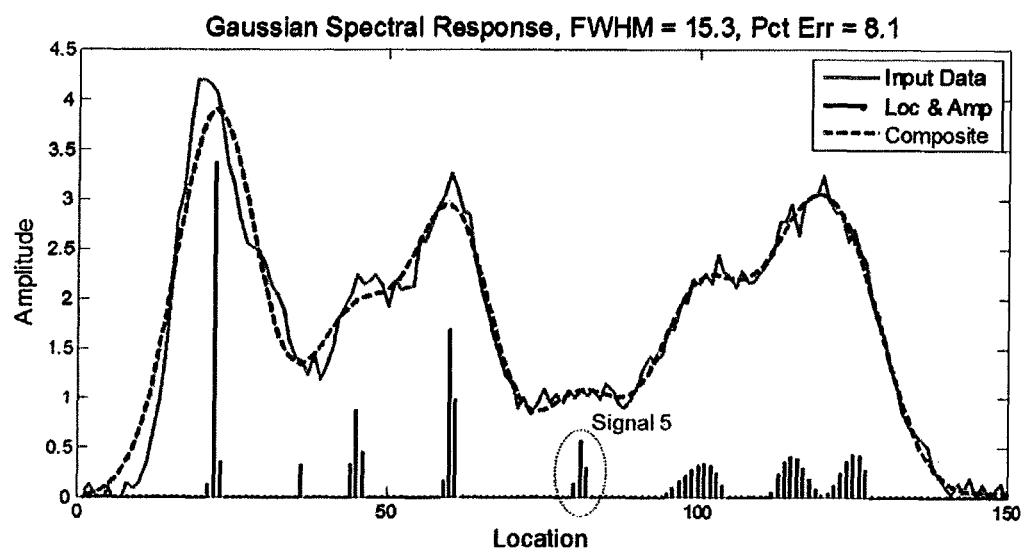
Figure 29:
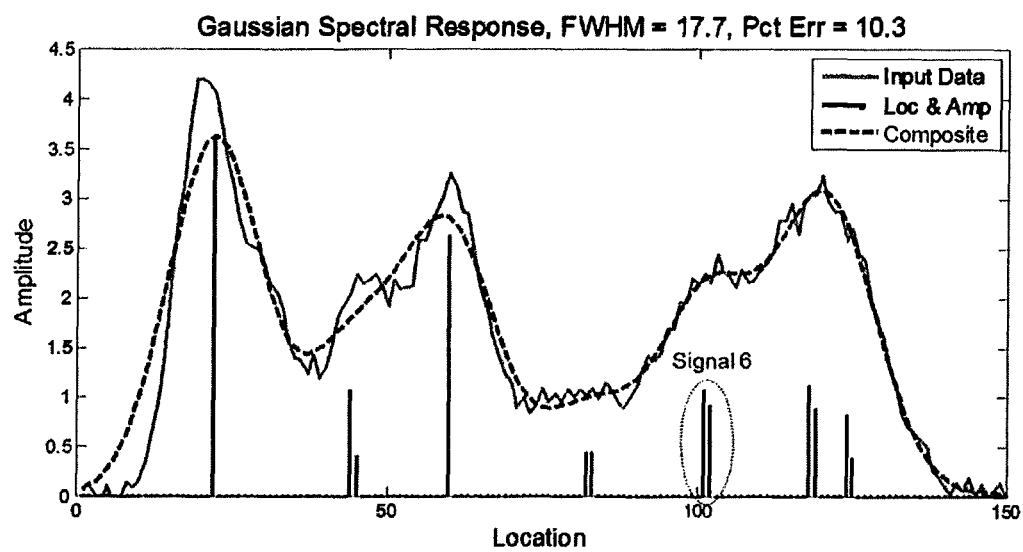
Figure 30:
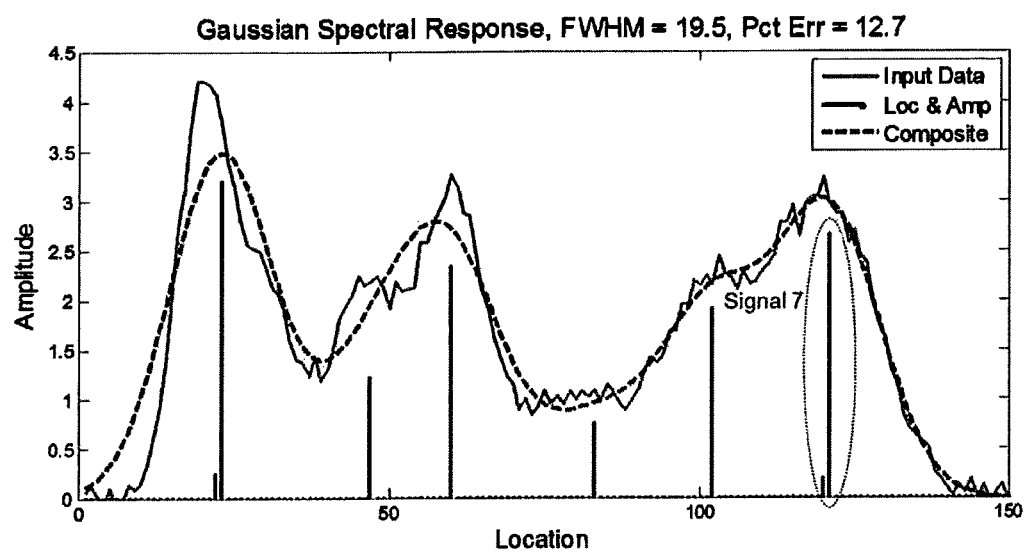
Figure 31:
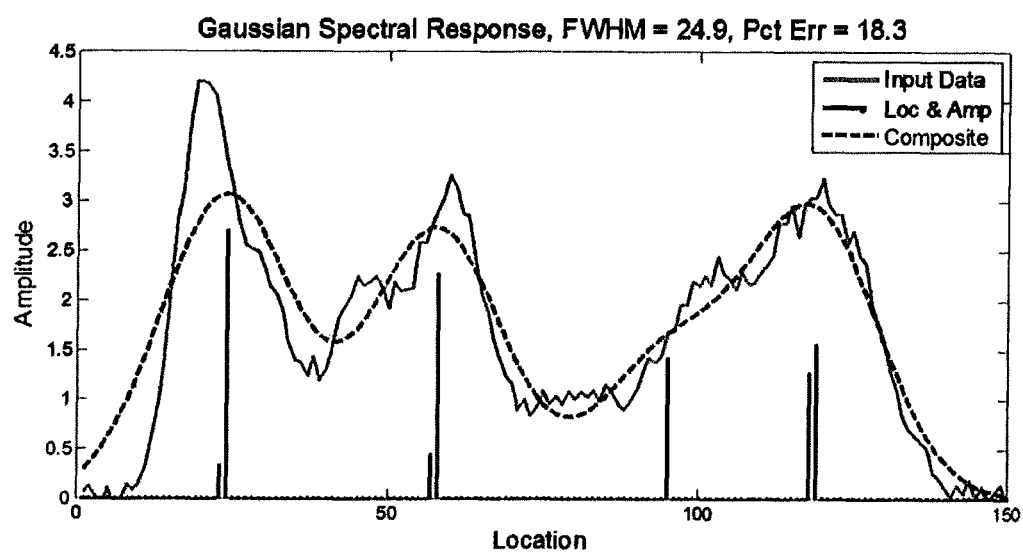

Again, the method 2000 is initiated by receiving the input trace signal data, an example of which is illustrated in FIG. 22. In step 2020, the trace signal data is subjected to the Phase I method (e.g., method 700 or method 2000 described herein) for each test signal width value in an initial set of multiple test signal width (i.e., FWHM) values. This results in a set of Spectral Response data sets (stem plot, location and amplitude) and composite fit traces for each of the initial set of test signal width values. FIGS. 23-31 show example Gaussian Spectral Response data sets (e.g., stem plot, location and amplitude) and composite Gaussian fit traces for each of an initial set of nine (9) test signal width values. The input test signal width value (e.g., FWHM) set may contain a minimum and maximum specified value, where the test signal width values may be evenly spaced or randomly spaced within the minimum and maximum value interval. For example, the test signal width values may vary over the interval by a specified percentage (e.g., 5% or 10% or 20%, etc.), e.g., proportionally spaced within the range. For example, FIG. 23 illustrates a Gaussian Spectral Response data set (e.g., stem plot showing location and amplitude), including amplitude groups, generated for a test signal width value of 8.5 (e.g., FWHM=8.5) and FIG. 24 illustrates a Gaussian Spectral Response data set, including amplitude groups, generated for a test signal width value of 10.3 (e.g., FWHM=10.3). The composite Gaussian fit traces are also shown in FIGS. 23 and 24 (and also FIGS. 25-31). The composite Gaussian trace fit represents the summation of each of the detected signal components (Gaussian traces) defined in the Gaussian Spectral Response data sets. FIG. 24 also shows the amplitude group labeled "Signal 1", which will be one of the final constituent signals determined at the end of the method 2000. Similarly, FIGS. 25-31 illustrate Gaussian Spectral Response data sets, including amplitude groups, generated for test signal width values of 10.9, 11.4, 13.2, 15.3, 17.7, 19.5, and 24.9, respectively (e.g., FWHM=10.9, 11.4, 13.2, 15.3, 17.7, 19.5, and 24.9, respectively). Each of these Gaussian Spectral Response data sets shown in FIGS. 23-31 represents the Gaussian content of the input signal trace data 2002 for the specified test signal width value (e.g., FWHM). FIGS. 25-30 also show the amplitude groups labeled "Signal 2", "Signal 3", "Signal 4", "Signal 5", "Signal 6", and "Signal 7", respectively, which will each be one of the final constituent signals determined at the end of the method 2000.

In step 2030, for each test signal width value, one or more preliminary constituent signals or detected signal components are determined and one or more signal characterization parameters for the preliminary constituent signals are determined from the Spectral Response data (stem plot, location and amplitude) for the test signal width value. The one or more preliminary constituent signals or detected signal components are determined by detecting amplitude (intensity value) groups, where an amplitude group is defined as one or more consecutive (no gaps) locations having non-zero positive amplitudes. In certain embodiments, the one or more signal characterizations parameters include at least a location of each preliminary constituent signal. In other embodiments, signal characterization parameters determined for each preliminary constituent signal may include a signal detection width value, a location and an amplitude value. A signal detection width may be defined as the width of the individual amplitude group, and may be determined by calculating a combined width of the one or more detected signal components making up the amplitude group. The signal location may be defined as the centroid of the amplitude group and may be determined by calculating the centroid of the one or more detected signal components making up the amplitude group. The signal amplitude may be defined as the summation of the individual amplitudes of the detected signal components within each amplitude group. In certain embodiments, the signal characterization parameters also may include an error value and a delta error value, or differential error value. In one embodiment, the error value for each amplitude group is determined by calculating the difference between the input trace and the composite trace fit (e.g., Gaussian trace fit) at each determined signal location in accordance with Equation 21 as follows:

$$Err_{(loc,k)} = \frac{100 \times \sum_{j=loc-2\sigma_k}^{loc+2\sigma_k} |y_j - yFit_{(j,k)}|}{\sum_{j=loc-2\sigma_k}^{loc+2\sigma_k} (y_j)} \qquad (21)$$

loc=detected signal location
$y_j$=input trace data point amplitude values
j=input trace data index
$\sigma_k$=test signal standard deviation
k=test signal standard deviation index
$yFit_{(j,k)}$=fit traces In certain embodiments, $yFit_{(j,k)}$ (set of fit traces) is calculated from Equation (15), above. The delta error (ΔErr) for each detected signal represents the differential error relative to the FWHM (or σ) and may be calculated utilizing Equation 22 as follows:

$$\Delta Err_{(loc,k)} = PreErr_{(loc,k)} + PostErr_{(loc,k)} - 2 \times Err_{(loc,k)} \qquad (22)$$

where:

$$PreErr_{(loc,k)} = \frac{100 \times \sum_{j=loc-2\sigma_k}^{loc+2\sigma_k} |y_j - yFit_{(j,k-\Delta k)}|}{\sum_{j=loc-2\sigma_k}^{loc+2\sigma_k} (y_j)} \qquad (23)$$

$$PostErr_{(loc,k)} = \frac{100 \times \sum_{j=loc-2\sigma_k}^{loc+2\sigma_k} |y_j - yFit_{(j,k+\Delta k)}|}{\sum_{j=loc-2\sigma_k}^{loc+2\sigma_k} (y_j)} \qquad (24)$$

Δk = test signal standard deviation index delta

The result of step 2030 is a set of detected signal component groups for each test signal width value, each of which contains a set of up to six (6) characteristic parameters: test signal width (e.g., FWHM), detection width, location, amplitude, error and delta error. The set of signals and the characteristic parameters may be stored to memory 1912 or a storage device 1914.

Figure 33:
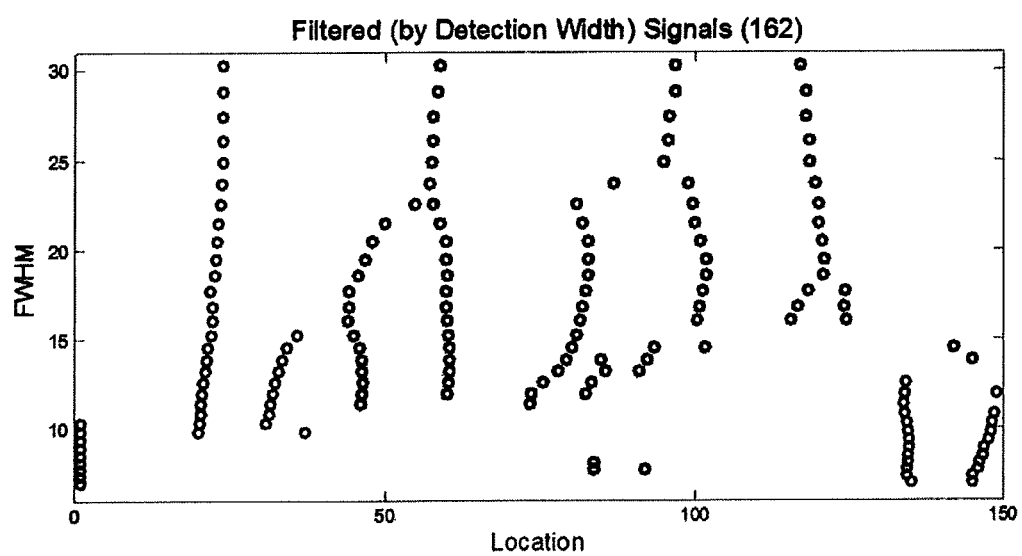
Figure 34:
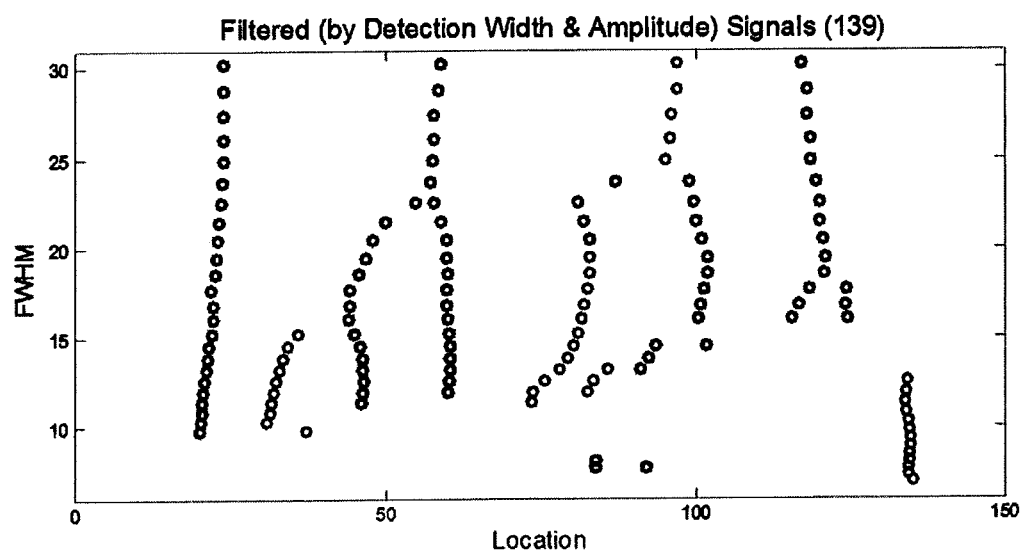
Figure 35:
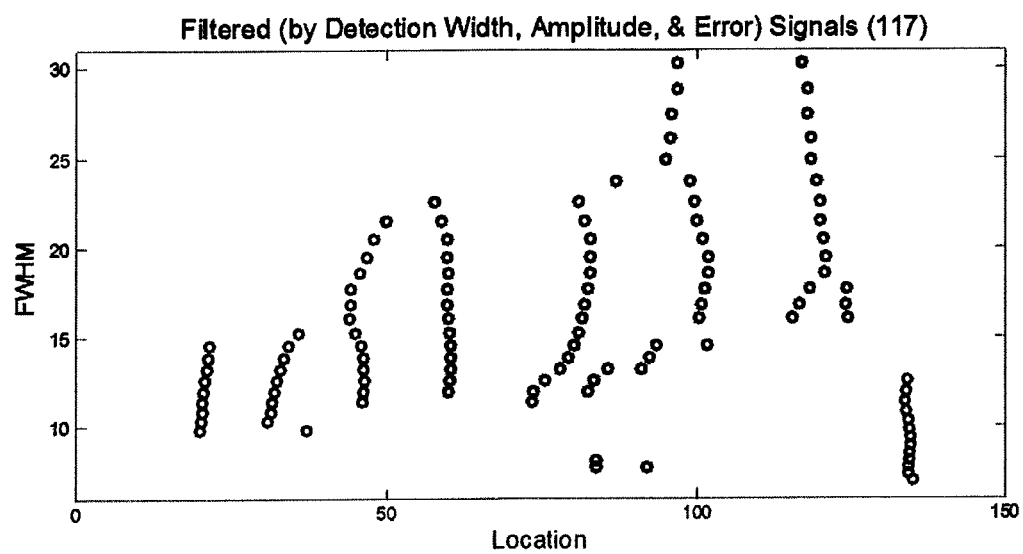
Figure 36:
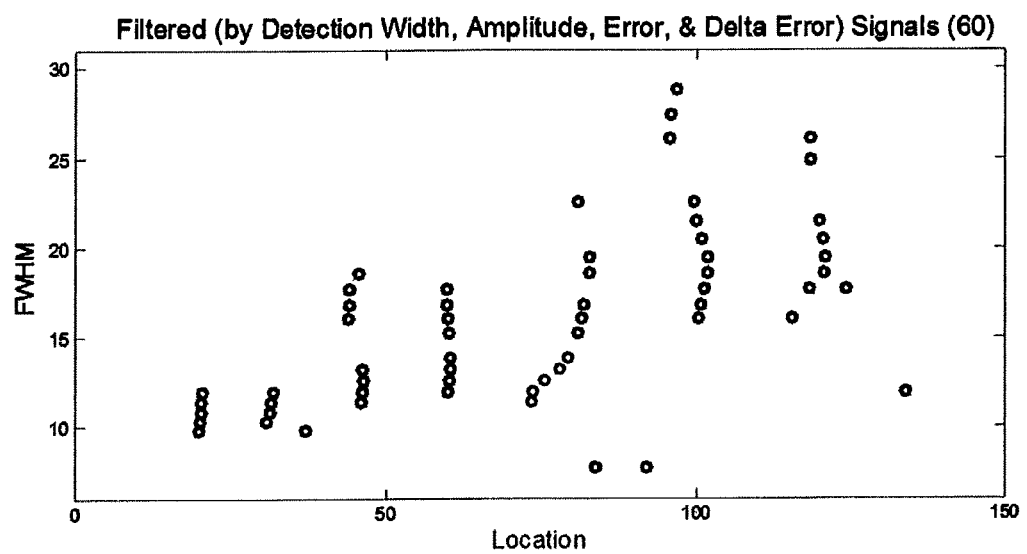
Figure 37:
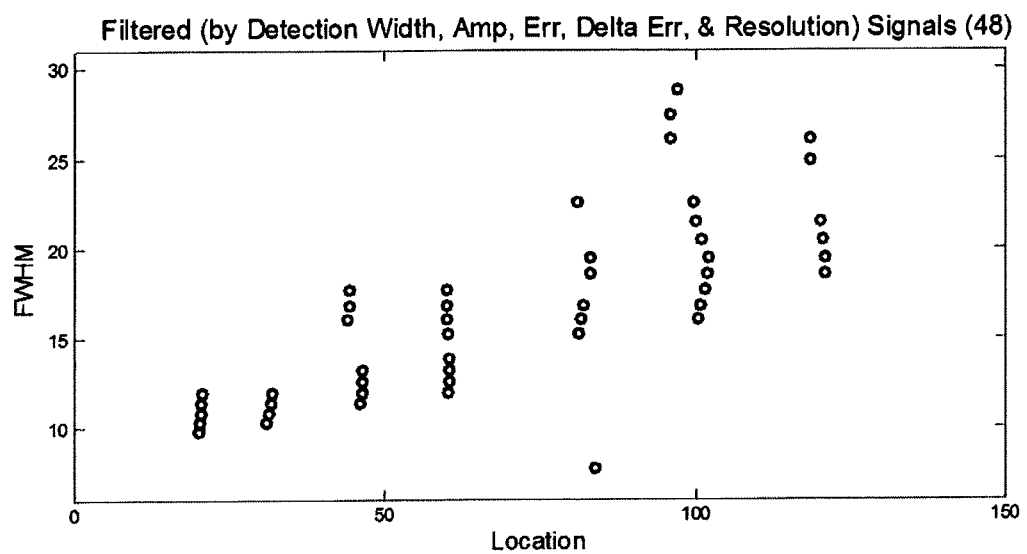

FIG. 32 illustrates an example of a scatter plot of all the (unfiltered) detected signal component groups, with the x-axis representing location and the y-axis representing the test signal width (e.g., FWHM). The scatter plot may be rendered on a display if desired. In optional step 2040, the detected signals are subjected to a series of one or more filters based upon one or more of the signal characterization parameters, e.g., detection width, amplitude, error, and delta error. In certain embodiments the detected signals may be subjected to a filter based upon a resolution value. FIGS. 33-37 illustrate examples of scatter plots of filtered, detected signal component groups according to filters applied to the detected signal component groups shown in FIG. 32. The first filter is based upon detection width, and when applied to the initial detected signal component groups, reduces the set of signals in this example from 228 to 162 as illustrated in FIG. 33. Signals with large detection widths relative to the sample FWHM are eliminated. The second filter is based upon amplitude and is applied to the previously filtered (based upon detection width) data and reduces the set of signals in this example from 162 to 139, as illustrated in FIG. 34. Signals with low amplitudes are eliminated. The third filter is based upon error and is applied to the previously filtered (based upon detection width and amplitude) data and reduces the set of signals in this example from 139 to 117, as illustrated in FIG. 35. Signals with large errors are eliminated. The fourth filter is based upon delta error, or differential error, and is applied to the previously filtered (based upon detection width, amplitude and error) data and reduces the set of signals in this example from 117 to 60, as illustrated in FIG. 36. Signals with small delta errors are eliminated. A fifth filter is based upon resolution and is applied to the previously filtered (based upon detection width, amplitude, error and delta error) data and reduces the set of signals in this example from 60 to 48, as illustrated in FIG. 37. Signals with low resolutions are eliminated, which may be calculated from Equation 25 as follows:

$$\text{Resolution} = \frac{\text{Signal Separation}}{4\sigma} \quad (25)$$

It should be noted that the signal separation is equal to the positive difference in the signal peak locations.

This final filtered set of detected signal component groups (e.g., as shown in FIG. 37) will then be reduced to a subset of signals representing the signal content of the input trace signal. It should be noted that as few or as many of the filters described above, or other filters, may be applied in any order as desired to reduce the number of signals for later processing in step 2050 and on.

Next, the set of detected signal component groups (signals) determined in step 2030, or if filtering is performed, the filtered signals generated in step 2040, are then subjected to a systematic and iterative selection process (combinatorial optimization), where at each iteration a selected subset of non-optimal signals is discarded and replaced with a more optimal subset of signals. The iterative process is initiated in step 2050 by selecting an initial set (or subset) of one or more detected signal component groups and calculating a best match or best fit for the initial set relative to the input trace. For example, the signal(s) from the largest FWHM sweep are selected and a percent fit error relative to the input trace is calculated, as illustrated in FIGS. 38A and 38B. FIG. 38A is a scatter plot that represents the selected signals from the first iteration (Iteration 1) of the selection process. In this example, only one (1) signal was selected. FIG. 38B shows synthesized data that represents the selected constituent signals, their composite, and the resultant percent error relative to the input trace from Iteration 1. Note that the composite signal shown (same as the constituent) is equivalent to the selected signal shown in FIG. 38A. The composite trace, which represents the summation of the selected constituent (e.g., Gaussian) signals, may be utilized to calculate the best match (e.g., percent fit error) relative to the input trace in accordance with Equation 26 as follows:

$$\text{Percent Error} = \frac{100 \times \sum_{1}^{N} |\text{Composite Trace} - \text{Input Trace}|}{\sum_{1}^{N} (\text{Input Trace})} \quad (26)$$

where N=number of trace data points.

In step 2060, an optimal combination of signals within the subset of signals is selected, wherein the optimal combination is defined as the signals within the subset that produce the lowest percent fit error. In the first iteration, the optimal combination may include only a single signal, especially if the initial set only includes a single signal, or it may include more than one signal if the initial set includes more than one signal. In step 2070, the signal set is updated to include a new signal that has not been used or included in a set during any iteration. The new signal is then added to the initial set, or the new signal replaces a signal in the initial set. For example, in one embodiment, a signal from the next decremented (i.e., smaller) FWHM sweep is selected as the new signal so that the following iterations may include signals from the previous FWHM sweep(s), as well as the next decremented (smaller) FWHM. In step 2080, the process repeats back to step 2060 until the signals for all test signal widths have been included in at least one (1) iteration. The process checks again in step 2060 to see if the newly included signal that was added to or replaced the existing signals results in a more optimal set (reduction in fit error). It should be noted that when multiple signals are within close proximity (based upon the specified resolution limit), the process may not allow simultaneous selection of those signals. This process is repeated at each FWHM decrement step until a final set (the most optimal set) of signals is determined (e.g., lowest fit error), as illustrated in the selected iteration examples shown in FIGS. 39-43. FIGS. 39A, 40A, 41A, 42A and 43A each show a scatter plot that represents filtered signals and selected signals from the fourth iteration (Iteration 4), seventh iteration (Iteration 7), twelfth iteration (Iteration 12), twentieth iteration (Iteration 20), and twenty-third iteration (Iteration 23), respectively, of the selection process. Also, FIGS. 39B, 40B, 41B, 42B and 43B each show synthesized data that represents the selected constituent signals, their composite, and the resultant percent error relative to the input trace from the fourth iteration (Iteration 4), seventh iteration (Iteration 7), twelfth iteration (Iteration 12), twentieth iteration (Iteration 20), and twenty-third iteration (Iteration 23), respectively. Each subsequent plot shows a decrease in percent error relative to the previous plotted iteration.

In step 2090, information about the final set of signals is output. For example, trace data synthesis engine 2006 may output signal peak locations and signal peak intensities and signal widths of one or more (previously unknown) signal components of the trace signal 2002 based on the final set of detected signal component groups and/or the trace data synthesis engine 2006 may render a visual representation of the overlapping signal components and/or a composite signal representing a combination of the signal components with or without a visual representation of the original trace signal data. FIGS. 43A and 43B illustrate graphical representations of final (e.g., optimal or near optimal) selected constituent signals and their representative characteristics.

Systems and methods for detecting, decoupling, and quantifying unresolved signals in trace signal data in the presence of noise, with no prior knowledge of the signal characteristics (e.g., signal peak location, amplitude and width) of the unresolved signals other than the general expected shape of the signal(s) (e.g., generalized signal model function such as Gaussian) are described above. These methods can determine the signal characteristics of a set of symmetrical signals. It can be desirable, however, to determine the signal characteristics of a set of asymmetrical signals.

According to another embodiment, a method is provided to determine the signal characteristics of a set of symmetrical signals as well as determine the signal characteristics of a set of asymmetrical signals and the amount of asymmetry present. This is accomplished by subjecting the input trace data to the modified Adaptive Signal Detection and Synthesis and the Spectral Response Synthesis methods with varying levels of asymmetry. The set of signals with the corresponding amount of asymmetry that best matches the input trace data is the one selected.

The ability to detect and characterize signals with unknown levels of asymmetry is significant in that data generated from spectroscopy, chromatography and electrophoresis often contain data with asymmetrically distributed signals. To determine accurate signal characteristics, it is important to know the amount of asymmetry present.

In some instances, it is desirable to determine asymmetry (skew) of the constituent signals determined in Phase I and/or Phase II of the method in conjunction with Phase I. In Phase III, optimal signal skew values (s) are determined. In one embodiment, a set of trial (test) signal skew values are processed individually in Phase I (method 700), or in Phase I in conjunction with Phase II (method 1000), and are evaluated together as a set to determine the optimal signal skew values (and the associated number of signals, locations, and amplitudes). For example, in one embodiment, a plurality of test signal skew values (s) are defined and Phase I process 700 (or Phase I process 700 and Phase II process 1000) is repeated for each of the plurality of test signal skew values (s) and the results of each Phase I output (or Phase I and Phase II output) are evaluated together to determine an optimal signal skew value or values for each of the one or more signal components of the trace signal. The test signal skew values may be defined automatically based on characteristics of the device or system that generated the trace signal data, or set by a user (e.g., by inputting specific test skew values, or a range of values, or selecting from a list of possible values or range of values).

A specific example of a methodology for Phase III, implemented in a matrix formulation, for determining one or more unknown signal components of trace signal data will now be described with reference to FIG. 44. FIG. 44 is a flow diagram of a matrix formulation of a signal width (sigma) determination method 4400 according to an embodiment. The method 4400 is initiated in step 4410 wherein the trace signal data is received. The trace signal data includes a plurality N of data points defined by x and y coordinates (i.e., the bandwidth of the trace signal data is defined by the x-dimension, or range, which may for example be frequency for spectrographic derived data, and the amplitudes are define by the y-dimension). FIG. 45 (top) illustrates a visual representation of an example of trace signal data displayed in a two dimensional x-y graph. As shown in the example at the top of FIG. 45, the trace signal data has a defined range e.g., (x=1 to x=N), and for purposes of description will be assumed to include 140 (N) data points At step 4420, the trace signal data is then subjected to the Phase I method (method 700) or the Phase I and the Phase II method (method 1000) together, with a modification to the Gaussian Model Equation, Equation 2 above, to a Bi-Gaussian Model Equation shown in Equations 27-29 below.

$$E_{(i,j)} = \begin{cases} e^{\frac{-[(x_j-\mu_i)/\sigma_1]^2}{2}} & (x_j < \mu_i) \\ e^{\frac{-[(x_j-\mu_i)/\sigma_2]^2}{2}} & (x_j \geq \mu_i) \end{cases} \quad (27)$$

$$\sigma_1 = \sigma\left(\frac{2s}{(s+1)}\right) \quad (28)$$

$$\sigma_2 = \sigma\left(\frac{2}{(s+1)}\right) \quad (29)$$

Where
$x_j$=trace data point locations
$\mu_i$=signal peak (mean) locations
$\sigma_1$=signal width (sigma) left of mean
$\sigma_2$=signal width (sigma) right of mean
s=asymmetry (skew) factor
i=1 to M (number of signals)
j=1 to N (number of data points)

These Bi-Gaussian equations allow for the evaluation of asymmetry in the signal width by utilization of the skew factor (s). It should be noted when s=1, the signal model is symmetrical as illustrated in FIG. 47, which shows a (symmetrical) Gaussian distribution. If s>1, meaning that $\sigma_1$ is greater than $\sigma_2$, the signal model is skewed as illustrated in FIG. 48. If s<1, meaning that $\sigma_1$ is less than $\sigma_2$, the signal model is skewed in the opposite direction.

A set of skew values can then be evaluated automatically to determine the amount of asymmetry present in the input trace data and to determine which skew value(s) produces the best set of constituent signals represented in the input trace data. For example, at step 4430, the best set of constituent signals may be determined as the set that produces the lowest percent fit error relative to the input trace (see, e.g., Equation 26).

FIG. 45 and FIG. 46 illustrate examples of processing a trace signal to determine constituent signals and the amount of asymmetry (skew) in the constituent signals according to method 4400 according to embodiments. FIG. 45 illustrates an example evaluation of asymmetrical Western Blot trace data using method 4400. It should be noted that the asymmetrical model (s≠1) produced the lowest percent fit error for this example. FIG. 46 illustrates an example evaluation of symmetrical trace data using method 4400. It should be noted that the symmetrical model (s=1) produced the lowest percent fit error for this example. In each of FIGS. 45 and 46, at least one run with s=1 is performed and at least one run with is performed. It should be appreciated, however, that multiple runs of different skew values (s) greater than and less than 1 are desired.

At step 4440, relevant signal characteristics of the determined constituent signals are processed or output. For example, the number of constituent signals, peak locations and/or amplitudes or intensities of the constituent signals, peak widths and/or skew values may be processed or output at step 4440. The determined signal characteristics may be used to describe or render a visualization of the signal content of the input trace signal data.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A processor-implemented method of processing a trace signal to determine one or more unknown signal components of the trace signal, the one or more unknown signal components having the same or dissimilar signal widths and the same or different asymmetry, the method comprising:
   receiving trace signal data, the trace signal data including a plurality N of data points and representing at least M signals within a bandwidth defining the trace data, wherein M is an integer greater than or equal to 1;
   for each of a plurality of asymmetry values:
      a) processing the trace signal data, separately for each of a plurality of test signal width values, to produce spectral response data including a signal location value and a signal intensity value for each of one or more detected signal components of the trace signal data for each of the plurality of test signal width values, wherein each test signal width value is a function of the asymmetry value;
      b) for each of the plurality of test signal width values:
         i) determining one or more detected signal component groups in the spectral response data based on the signal intensity values of the one or more detected signal components, each detected signal component group comprising one or more of the detected signal components corresponding to one or more consecutive signal locations having a non-zero, positive signal intensity value; and
         ii) determining one or more signal characterization parameters for each of the one or more detected signal component groups, wherein the one or more signal characterization parameters includes at least a location of each of the one or more detected signal component groups, and wherein the location of each of the one or more detected signal component groups is determined by calculating a centroid of the locations of the one or more detected signal components making up the detected signal component group;
      and thereafter
      c) performing an iterative combinatorial optimization process on all or a subset of the detected signal component groups determined for all test signal width values, based on one or more of the signal characterization parameters of the one or more detected signal component groups, to determine a final set of one or more detected signal component groups having a best match relative to the trace signal data; and
   determining, from among all the final sets of one or more detected signal component groups, an optimal final set that produces the lowest percent fit error relative to the trace signal data; and
   outputting locations, intensities and signal widths of one or more signal components of the trace signal data based on the optimal final set of one or more detected signal component groups.

2. The method of claim 1, wherein a test width value includes a first test width value, $\sigma_1$, defining a width to a left side of the signal location value and a second test width value, $\sigma_2$, defining a width to the right of the signal location value.

3. The method of claim 2, wherein $$\sigma_1 = \sigma\left(\frac{2s}{(s+1)}\right), \sigma_2 = \sigma\left(\frac{2}{(s+1)}\right),$$

and wherein s is the asymmetry value.

4. The method of claim 1, wherein the performing the iterative combinatorial optimization process includes:
   selecting an initial set of one or more detected signal component groups; and
   at each iteration:
      i) determining a composite signal comprising the initial set of one or more detected signal component groups;
      ii) determining a percent fit error for the composite signal relative to the trace signal data;

iii) selecting an unused detected signal component group, wherein the unused detected signal component group is a detected signal component group that has not been included in the initial set of one or more detected signal component groups during any iteration;

iv) adding the unused detected signal component group to the initial set, or replacing one of the detected signal component groups in the initial set with the unused detected signal component group to form an altered set of one or more detected signal component groups; and v) determining the final set of one or more detected signal component groups by iteratively repeating steps i) through iv) using the altered set of one or more detected signal component groups as the initial set of one or more detected signal component groups until all detected signal component groups in the all or the subset of the detected signal component groups has been used in at least one iteration of step iv), wherein the final set corresponds to the altered set having the best match as determined in step ii).

5. The method of claim 4, wherein the performing the iterative combinatorial optimization process further includes filtering the detected signal component groups to be processed based on one or more of the signal characterization parameters.

6. The method of claim 1, wherein the processing the trace signal data to produce the spectral response data for a specified test signal width value includes:

a) defining an initial set of signal components to be the number N of data points, wherein initial signal locations for each of the signal components of the initial set of signal components correspond to the locations within the bandwidth of the number N of data points, wherein all signal components in the initial set of signal components are assigned the specified test signal width value;

b) simultaneously performing a numerical method signal extraction calculation on each signal component in the initial set of signal components;

c) determining a signal amplitude value for each signal component of the initial set of signal components based on the extraction calculation;

d) removing from the initial set of signal components, or attenuating, each signal component determined to have a negative signal amplitude value based on the extraction calculation to produce an adjusted set of signal components; and e) determining a final set of signal components by iteratively repeating steps b)-d) using the adjusted set of signal components as the initial set of signal components until no signal component has a negative amplitude value based on the extraction calculation, wherein the final set of signal components correspond to the one or more detected signal components for the specified test signal width value.

7. The method of claim 6, wherein the numerical method signal extraction calculation includes a conjugate gradient method, a Generalized Minimum Residual method, a Newton's method, a Broyden's method or a Gaussian elimination method.

8. The method of claim 1, wherein the trace signal data includes noise.

9. The method of claim 1, wherein all unknown signal components in the trace data are assumed to have the same curve profile type selected from the group consisting of a Gaussian profile, a bi-Gaussian profile, an exponentially modified Gaussian profile, a Haarhoff-van der Linde profile, a Lorentzian profile and a Voigt profile.

10. The method of claim 1, wherein the plurality of asymmetry values include a minimum specified value and a maximum specified value, and wherein each of the plurality of asymmetry values is proportionally spaced within a range defined by the minimum specified value and the maximum specified value.

11. The method of claim 1, wherein outputting locations, intensities and signal widths of the one or more signal components of the trace signal based on the optimal final set of signal components includes rendering a visual output of the one or more signal components of the trace signal with a visual representation of the trace signal data.

12. A non-transitory computer readable medium storing code, which when executed by one or more processors cause the one or more processors to implement a method of processing a trace signal to determine one or more unknown signal components of the trace signal, the unknown signal components having the same or dissimilar signal widths and the same or dissimilar asymmetry, the code including instructions to:

receive trace signal data, the trace signal data including a plurality N of data points and representing at least M signals within a bandwidth defining the trace data, wherein M is an integer greater than or equal to 1;

for each of a plurality of asymmetry values: a) process the trace signal data, separately for each of a plurality of test signal width values, to produce spectral response data including a signal location and a signal intensity value for each of one or more detected signal components of the trace signal data for each of the plurality of test signal width values, wherein each test signal width value is a function of the asymmetry value;

b) for each of the plurality of test signal width values:

i) determine one or more detected signal component groups in the spectral response data based on the signal intensity values of the one or more detected signal components, each detected signal component group comprising one or more of the detected signal components corresponding to one or more consecutive signal locations having a non-zero, positive signal intensity value; and ii) determine one or more signal characterization parameters for each of the one or more detected signal component groups, wherein the one or more signal characterization parameters includes at least a location of each of the one or more detected signal component groups, and wherein the location of each of the one or more detected signal component groups is determined by calculating a centroid of the locations of the one or more detected signal components making up the detected signal component group; and thereafter c) perform an iterative combinatorial optimization process on all or a subset of the detected signal component groups determined for all test signal width values, based on one or more of the signal characterization parameters of the one or more detected signal component groups, to determine a final set of one or more detected signal component groups having a best match relative to the trace signal data; and determine, from among all the final sets of one or more detected signal component groups, an optimal final set that produces the lowest percent fit error relative to the trace signal data; and output locations, intensities and signal widths of one or more signal components of the trace signal data based on the optimal final set of one or more detected signal component groups.

13. The non-transitory computer readable medium of claim 12, wherein the instructions to perform the iterative combinatorial optimization process includes instructions to: select an initial set of one or more detected signal component groups; and at each iteration:
   i) determine a composite signal comprising the initial set of one or more detected signal component groups;
   ii) determine a percent fit error for the composite signal relative to the trace signal data;
   iii) select an unused detected signal component group, wherein the unused detected signal component group is a detected signal component group that has not been included in the initial set of one or more detected signal component groups during any iteration;
   iv) add the unused detected signal component group to the initial set, or replace one of the detected signal component groups in the initial set with the unused detected signal component group to form an altered set of one or more detected signal component groups; and
   v) determine the final set of one or more detected signal component groups by iteratively repeating steps i) through iv) using the altered set of one or more detected signal component groups as the initial set of one or more detected signal component groups until all detected signal component groups in the all or the subset of the detected signal component groups has been used in at least one iteration of step iv), wherein the final set corresponds to the altered set having the best match as determined in step ii).

14. The non-transitory computer readable medium of claim 12, wherein the instructions to perform the iterative combinatorial optimization process further includes instructions to filter the detected signal component groups to be processed based on one or more of the signal characterization parameters.

15. The non-transitory computer readable medium of claim 12, wherein the trace signal data includes noise.

16. The non-transitory computer readable medium of claim 12, wherein the instructions to process the trace signal data to produce the spectral response data for a specified test signal width value includes instructions to:
   a) define an initial set of signal components to be the number N of data points, wherein initial signal locations for each of the signal components of the initial set of signal components correspond to the locations within the bandwidth of the number N of data points, wherein all signal components in the initial set of signal components are assigned the specified test signal width value;
   b) simultaneously perform a numerical method signal extraction calculation on each signal component in the initial set of signal components;
   c) determine a signal amplitude value for each signal component of the initial set of signal components based on the extraction calculation;
   d) remove from the initial set of signal components, or attenuate, each signal component determined to have a negative signal amplitude value based on the extraction calculation to produce an adjusted set of signal components; and
   e) determine a final set of signal components by iteratively repeating b)-d) using the adjusted set of signal components as the initial set of signal components until no signal component has a negative amplitude value based on the extraction calculation, wherein the final set of signal components correspond to the one or more detected signal components for the specified test signal width value.

17. The non-transitory computer readable medium of claim 16, wherein the numerical method signal extraction calculation includes a conjugate gradient method, a Generalized Minimum Residual method, a Newton's method, a Broyden's method or a Gaussian elimination method.

18. The non-transitory computer readable medium of claim 12, wherein a test width value includes a first test width value, $\sigma 1$, defining a width to a left side of the signal location value and a second test width value, $\sigma 2$, defining a width to the right of the signal location value.

19. The non-transitory computer readable medium of claim 18, wherein $$\sigma_1 = \sigma\left(\frac{2s}{(s+1)}\right), \sigma_2 = \sigma\left(\frac{2}{(s+1)}\right),$$

and wherein s is the asymmetry value.

20. The non-transitory computer readable medium of claim 12, wherein the instructions to output locations, intensities and signal widths of the one or more signal components of the trace signal based on the final set of signal components includes instructions to render a visual output of the one or more signal components of the trace signal with a visual representation of the trace signal data.

21. A processing device that processes a trace signal to determine one or more unknown signal components of the trace signal, the device comprising:
   a processor; and
   a memory storing code executable by the processor;
   wherein the code includes instructions, which when executed by the processor, cause the processor to:
   receive trace signal data, the trace signal data including a plurality N of data points and representing at least M signals within a bandwidth defining the trace data, wherein M is an integer greater than or equal to 1;
   for each of a plurality of asymmetry values:
      a) process the trace signal data, separately for each of a plurality of test signal width values, to produce spectral response data including a signal location and a signal intensity value for each of one or more detected signal components of the trace signal data for each of the plurality of test signal width values, wherein each test signal width value is a function of the asymmetry value;
      b) for each of the plurality of test signal width values:
         i) determine one or more detected signal component groups in the spectral response data based on the signal intensity values of the one or more detected signal components, each detected signal component group comprising one or more of the detected signal components corresponding to one or more consecutive signal locations having a non-zero, positive signal intensity value; and
         ii) determine one or more signal characterization parameters for each of the one or more detected signal component groups, wherein the one or more signal characterization parameters includes at least a location of each of the one or more detected signal component groups, and wherein the loca-tion of each of the one or more detected signal component groups is determined by calculating a centroid of the locations of the one or more detected signal components making up the detected signal component group; and thereafter c) perform an iterative combinatorial optimization process on all or a subset of the detected signal component groups determined for all test signal width values, based on one or more of the signal characterization parameters of the one or more detected signal component groups, to determine a final set of one or more detected signal component groups having a best match relative to the trace signal data; and determine, from among all the final sets of one or more detected signal component groups, an optimal final set that produces the lowest percent fit error relative to the trace signal data; and output locations, intensities and signal widths of one or more signal components of the trace signal data based on the optimal final set of one or more detected signal component groups.

22. The processing device of claim 21, further including a display, wherein the instructions to output locations, intensities and signal widths of the one or more signal components of the trace signal based on the optimal final set of signal components includes instructions to render, on the display, a visual output of the one or more signal components of the trace signal with a visual representation of the trace signal data.

23. The processing device of claim 21, wherein a test width value includes a first test width value, σ1, defining a width to a left side of the signal location value and a second test width value, σ2, defining a width to the right of the signal location value.

24. The processing device of claim 23, wherein $$\sigma_1 = \sigma\left(\frac{2s}{(s+1)}\right), \sigma_2 = \sigma\left(\frac{2}{(s+1)}\right),$$

and wherein s is the asymmetry value.

* * * * *